United States Patent
Davis et al.

(10) Patent No.: US 9,518,249 B2
(45) Date of Patent: *Dec. 13, 2016

(54) CELL CARRIER, ASSOCIATED METHODS FOR MAKING CELL CARRIER AND CULTURING CELLS USING THE SAME

(71) Applicant: General Electric Company, Schenectady, NY (US)

(72) Inventors: Brian Michael Davis, Albany, NY (US); Evelina Roxana Loghin, Rexford, NY (US); Kenneth Roger Conway, Clifton Park, NY (US); Andrew Arthur Paul Burns, Niskayuna, NY (US); David Gilles Gascoyne, Niskayuna, NY (US)

(73) Assignee: GENERAL ELECTRIC COMPANY, Niskayuna, NY (US)

(*) Notice: Subject to any disclaimer, the term of this patent is extended or adjusted under 35 U.S.C. 154(b) by 153 days.

This patent is subject to a terminal disclaimer.

(21) Appl. No.: 13/839,049

(22) Filed: Mar. 15, 2013

(65) Prior Publication Data

US 2014/0186946 A1 Jul. 3, 2014

Related U.S. Application Data

(63) Continuation-in-part of application No. 12/970,735, filed on Dec. 16, 2010.

(51) Int. Cl.
*C12N 5/0735* (2010.01)
*C12N 5/00* (2006.01)

(52) U.S. Cl.
CPC ....... *C12N 5/0068* (2013.01); *C12N 2501/999* (2013.01); *C12N 2533/30* (2013.01); *C12N 2533/52* (2013.01); *C12N 2533/90* (2013.01); *C12N 2535/10* (2013.01); *C12N 2537/00* (2013.01); *Y10T 156/1039* (2015.01)

(58) Field of Classification Search
CPC . C12N 5/0068; C12N 5/0075; C12N 2533/12; C12N 2533/14; C12N 2533/30; C12N 2533/50; C12N 2535/00
USPC .................................................. 435/395, 402
See application file for complete search history.

(56) References Cited

U.S. PATENT DOCUMENTS

| | | |
|---|---|---|
| 4,801,475 A | 1/1989 | Halpern et al. |
| 4,906,237 A | 3/1990 | Johansson et al. |
| 5,284,766 A | 2/1994 | Okano et al. |
| 5,449,620 A | 9/1995 | Khillan |
| 5,707,859 A | 1/1998 | Miller et al. |
| 5,763,548 A | 6/1998 | Matyjaszewski et al. |
| 5,800,412 A | 9/1998 | Zhang et al. |
| 6,121,371 A | 9/2000 | Matyjaszewski et al. |
| 6,190,913 B1* | 2/2001 | Singh ..................... 435/394 |
| 6,627,314 B2 | 9/2003 | Matyjaszewski et al. |
| 6,720,469 B1 | 4/2004 | Curtis et al. |
| 6,777,227 B2 | 8/2004 | Ricci et al. |
| 6,790,919 B2 | 9/2004 | Matyjaszewski et al. |
| 6,861,103 B2 | 3/2005 | Chang et al. |
| 7,052,776 B2 | 5/2006 | Fanta et al. |
| 7,354,704 B2 | 4/2008 | Malin et al. |
| 8,148,111 B2 | 4/2012 | Kurokawa et al. |
| 8,241,907 B2 | 8/2012 | Shogbon et al. |
| 2002/0028493 A1 | 3/2002 | de Bruijn et al. |
| 2002/0081726 A1 | 6/2002 | Russell et al. |
| 2003/0003554 A1 | 1/2003 | Miller et al. |
| 2003/0036196 A1 | 2/2003 | Okano et al. |
| 2003/0162287 A1 | 8/2003 | Yamamoto et al. |
| 2003/0219824 A1 | 11/2003 | Malin et al. |
| 2004/0214326 A1 | 10/2004 | Cousins et al. |
| 2005/0054101 A1 | 3/2005 | Felder et al. |
| 2006/0165625 A1 | 7/2006 | Verrall et al. |
| 2006/0205071 A1 | 9/2006 | Hasson et al. |
| 2008/0009064 A1 | 1/2008 | Ronfard et al. |
| 2008/0026464 A1 | 1/2008 | Borenstein et al. |
| 2008/0187995 A1 | 8/2008 | Murphy et al. |
| 2008/0199959 A1 | 8/2008 | Algotsson et al. |
| 2008/0208351 A1 | 8/2008 | Besenbacher et al. |
| 2009/0047260 A1 | 2/2009 | Van Dyke |
| 2009/0069904 A1 | 3/2009 | Picha |
| 2009/0098183 A1 | 4/2009 | Detamore et al. |
| 2009/0228027 A1 | 9/2009 | Yamanaka et al. |
| 2009/0248145 A1* | 10/2009 | Chan et al. .............. 623/1.41 |
| 2009/0248157 A1 | 10/2009 | Dalby et al. |
| 2009/0311735 A1 | 12/2009 | Crook et al. |
| 2010/0093053 A1 | 4/2010 | Oh et al. |
| 2010/0124781 A1 | 5/2010 | Nelson |
| 2010/0136647 A1 | 6/2010 | Algotsson et al. |
| 2010/0197013 A1 | 8/2010 | Kamp et al. |
| 2010/0291674 A1 | 11/2010 | Beese et al. |

(Continued)

FOREIGN PATENT DOCUMENTS

| | | |
|---|---|---|
| DE | 102006012960 A1 | 9/2007 |
| EP | 0382214 B1 | 5/1995 |

(Continued)

OTHER PUBLICATIONS

Collignon et al., "Integrity™ Xpansion™ Multiplate Bioreactor: The Scalable Solution for Adherent Stem Cell Expansion", ATMI LifeSciences, 2010, 1 Page.

(Continued)

*Primary Examiner* — Antonio Galisteo Gonzalez
(74) *Attorney, Agent, or Firm* — Fletcher Yoder, P.C.

(57) ABSTRACT

A carrier for expansion of pluripotent stem cells is provided, wherein the carrier comprises a substrate comprising one or more outer surfaces, wherein the one or more outer surfaces are modified with gas plasma treatment, and one or more structured indentations on one or more of the outer surfaces. The carrier has a length at least about 0.2 mm, a width at least about 0.2 mm, and a height in a range from about 0.05 mm to 1.2 mm and each of the structured indentations has a major axis in a range from about 0.1 mm to 0.5 mm, a minor axis in a range from about 0.1 mm to 0.5 mm and a depth in a range from about 0.025 mm to about 0.5 mm. A method of making the carrier, and culturing stromal cells using the same carrier are also provided.

27 Claims, 17 Drawing Sheets

(56) References Cited

U.S. PATENT DOCUMENTS

| | | | |
|---|---|---|---|
| 2010/0304482 | A1 | 12/2010 | Deshayes et al. |
| 2010/0330674 | A1 | 12/2010 | Rubinsztajn et al. |
| 2011/0027889 | A1 | 2/2011 | McCarthy et al. |
| 2011/0076764 | A1 | 3/2011 | Rubinsztain et al. |
| 2011/0104732 | A1 | 5/2011 | Lucic et al. |
| 2011/0129919 | A1 | 6/2011 | Oh et al. |
| 2011/0160869 | A1 | 6/2011 | Duch et al. |
| 2011/0207209 | A1 | 8/2011 | Hammons et al. |
| 2011/0207216 | A1 | 8/2011 | Martin et al. |
| 2011/0275154 | A1 | 11/2011 | Martin et al. |
| 2012/0045830 | A1 | 2/2012 | Green et al. |
| 2012/0052579 | A1 | 3/2012 | Shannon et al. |
| 2012/0058556 | A1 | 3/2012 | Fabian et al. |
| 2012/0058561 | A1 | 3/2012 | Sato |
| 2012/0156772 | A1 | 6/2012 | Miller et al. |
| 2012/0156773 | A1 | 6/2012 | Smith et al. |
| 2012/0156777 | A1 | 6/2012 | Rangarajan et al. |
| 2012/0219531 | A1 | 8/2012 | Oh et al. |
| 2013/0210140 | A1 | 8/2013 | Burns et al. |
| 2014/0051163 | A1 | 2/2014 | Healy et al. |
| 2014/0356949 | A1 | 12/2014 | Davis et al. |

FOREIGN PATENT DOCUMENTS

| | | |
|---|---|---|
| GB | 1079391 A | 8/1967 |
| JP | 2004018556 A | 1/2004 |
| JP | 2010057485 A | 3/2010 |
| JP | 2010136706 A | 6/2010 |
| WO | 9932595 A1 | 7/1999 |
| WO | 0070406 A1 | 11/2000 |
| WO | 0162803 A2 | 8/2001 |
| WO | 01192359 A1 | 12/2001 |
| WO | 03055967 A1 | 7/2003 |
| WO | 2004090506 A3 | 6/2005 |
| WO | 2006033935 A2 | 3/2006 |
| WO | WO 2007125288 A1 * | 11/2007 |
| WO | 2008106771 A1 | 9/2008 |
| WO | 2008140295 A1 | 11/2008 |
| WO | 2009034186 A2 | 3/2009 |
| WO | WO 2009105570 A2 * | 8/2009 |
| WO | 2010094944 A1 | 8/2010 |
| WO | 2011106032 A1 | 9/2011 |
| WO | 2011147930 A1 | 12/2011 |
| WO | 2012069841 A1 | 5/2012 |

OTHER PUBLICATIONS

Ueda et al., "Substrates for Human Pluripotent Stem Cell Cultures in Conditioned Medium of Mesenchymal Stem Cells", Journal of Biomaterials Science, Polymer Edition, vol. 23, Issue 1-4, Apr. 13, 2012, pp. 153-165.

Manbachi et al. "Microcirculation within Grooved substrates regulates Cell positioning and Cell Docking inside Microfluidic Channels", Lab Chip, pp. 747-754, May 2008.

BD Biosciences, BD Biocoat—Dish 35MM PLL 5PAC 20CAS, 2010.

Fujita et al., "Time-lapse observation of cell alignment on nanogrooved patterns", Journal of Royal Society Interface, vol. No. 6, pp. S269-S277; Feb. 25, 2009.

Funakoshi General Catalog 2005-2006 devices edition, pp. VIII-IX, Dec. 22, 2005.

Moeller et al., "A microwell Array system for stem cell culture", pp. 752-763, Nov. 14, 2007.

Cha et al., "Construction of Functional Soft Tissues From Premodulated Smooth Muscle Cells Using a Bioreactor System", Artificial Organs, vol. No. 30, Issue No. 9, pp. 704-707, Sep. 2006.

Cha et al., "Time-dependent Modulation of Alignment and Differentiation of Smooth Muscle Cells Seeded on a Porous Substrate Undergoing Cyclic Mechanical Strain", Artificial Organs, vol. No. 30, Issue No. 4, pp. 250-258, Apr. 2006.

Khorasani et al., "Plasma Surface Modification of Poly (l-Lactic acid) and Poly (lactic-co-glycolic acid) Films for Improvement of Nerve Cells Adhesion", Radiation Physics and Chemistry, pp. 280-287, vol. No. 77, Issue No. 3, Mar. 2008.

Kohen et al., "Characterization of Matrigel interfaces during Defined Human Embryonic Stem Cell Culture", Biointerphases, pp. 69-79, vol. No. 4, Issue No. 4, Dec. 2009.

Korin et al., "Design of Well and Groove Microchannel Bioreactors for Cell Culture", Biotechnology and Bioengineering, vol. No. 102, Issue No. 4, pp. 1222-1230, May 1, 2009.

Lee et al., "Response of human chondrocytes on polymer surfaces with different micropore sizes for tissue-engineered cartilage", J Appl Polym Sci., vol. No. 92, pp. 2784-2790, 2004.

Jiang et al., "Fabrication of plastic microlens arrays using hybrid extrusion rolling embossing with a metallic cylinder mold fabricated using dry film resist", Optics Express, vol. No. 15, Issue No. 19, pp. 12088, Jan. 1, 2007.

Khabiry et al.; "Cell Docking in Double Grooves in a Microfluidic channel", 9 pages, 2009.

Focke et al. "Lab-on-a-Foil: microfluidics on thin and flexible films", Lab on a Chip, vol. No. 10, pp. 1365-1386; Mar. 19, 2010.

McMurray et al., "Nanoscale surfaces for the long-term maintenance of mesenchymal stem cell phenotype and multipotency", Nature Materials, vol. No. 10, 8 pages, Aug. 2011.

Lindstrom et al., "High-Density Microwell Chip for Culture and Analysis of Stem Cells", PLoS One, vol. No. 4, Issue No. 9, pp. 1-9, Sep. 30, 2009.

Satoh et al., "Cultivation of Human Induced Pluripotent Stem Cells with Controlled Aggregate Size and Geometrical Arrangement by Inverting Microwell Array Chip", 17th International Conference on Miniaturized Systems for Chemistry and Life Sciences, pp. 1701-1703, Issue No. 27-31, Oct. 2013.

Kessel et al., "Thermoresponsive PEG-based polymer Layers: Surface characterization with AFM force easurements", Langxmuir, vol. No. 26, Issue No. 5, pp. 3462-3467, 2010.

Thormann et al., "Interactions between a Polystyrene Particle and Hydrophilic and Hydrophobic Surfaces in Aqueous Solutions", Langmuir, vol. No. 24, Issue No. 14, pp. 7278-7284, 2008.

Huang et al., "Fast fabrication of integrated surface-relief and particle-diffusing plastic diffuser by use of a hybrid extrusion roller embossing process", Optics Express, vol. No. 16, Issue No. 1, pp. 440, Jan. 2008.

Kooten et al., "Plasma-treated polystyrene surface: model surfaces for studying cell-biomaterial interactions", Biomaterials; vol. No. 25, pp. 1735-1747, 2004.

Welten et al., "Roll-to-Roll Hot Embossing of Microstructures", Design Test Integration and Packaging of MEMS/MOEMS (DTI P), pp. 326-331, 2010.

Welten et al., "Investigations on reel-to-reel hot embossing", The international journal of advanced technology, springer, berlin, DE, vol. No. 1-4, 24, pp. 73-80, Feb. 2009.

Wave Bioreactor Catalog2006, Wave Europe, pp. 1-13, 2006.

Yeo et al., "Micro-fabrication of polymeric devices using hot roller embossing"; Microelectronic Engineering, vol. No. 86, pp. 933-936, Dec. 2008.

International Search Report and Written Opinion issued in connection with related PCT Application No. PCT/EP2011/073065 dated Apr. 23, 2012.

International Search Report and Written Opinion issued in connection with related PCT Application No. PCT/EP2011/073061 dated May 2, 2012.

International Search Report and Written Opinion issued in connection with related PCT Application No. PCT/EP2011/073066 dated May 7, 2012.

International Search Report and Written Opinion issued in connection with related PCT Application No. PCT/EP2011/073064 on May 9, 2012.

Unofficial English translation of Office Action and Search Report issued in connection with related CN Application No. 201180060701.9 on May 6, 2014.

Unofficial English translation of Office Action issued in connection with related CN Application No. 201180060701.9 on Jul. 6, 2015.

(56) References Cited

OTHER PUBLICATIONS

Unofficial English translation of Office Action issued in connection with related JP Application No. 2013543815 on Dec. 15, 2015.

* cited by examiner

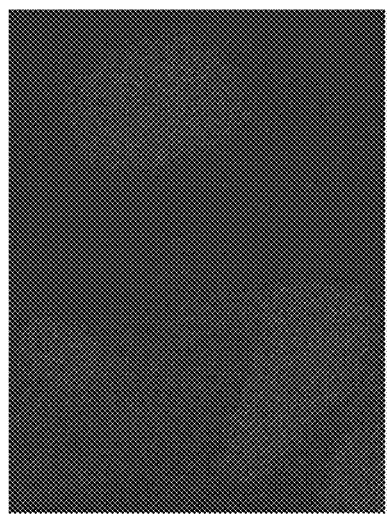
FIG. 8A
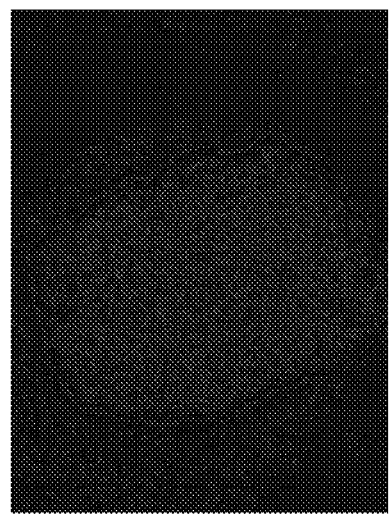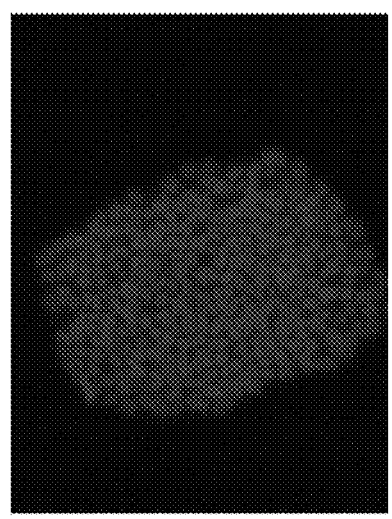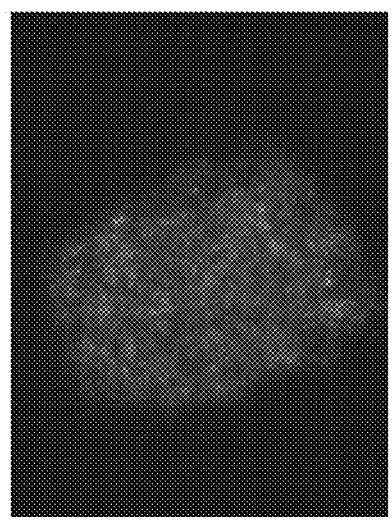
FIG. 8D
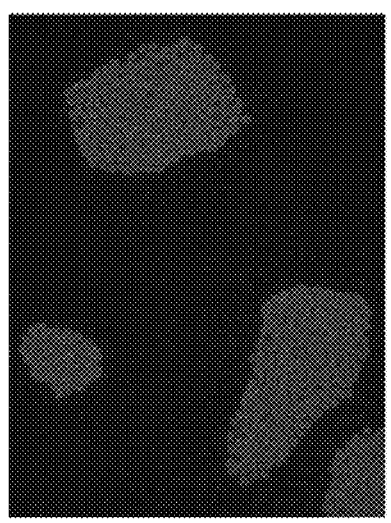
FIG. 8B
FIG. 8E
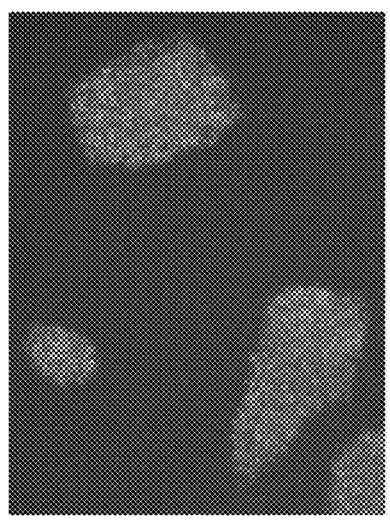
FIG. 8C
FIG. 8F

CELL CARRIER, ASSOCIATED METHODS FOR MAKING CELL CARRIER AND CULTURING CELLS USING THE SAME

CROSS REFERENCE TO RELATED APPLICATIONS

This application is a continuation-in-part of U.S. patent application Ser. No. 12/970,735, entitled "Cell carrier, associated methods for making cell carrier and culturing cells using the same", filed Dec. 16, 2010; which is herein incorporated by reference.

FIELD

The invention relates to cell carriers for culturing pluripotent stem cells, and associated methods for making and using the cell carriers. More particularly, the invention relates to polymer based cell carriers with surface modification to expand undifferentiated pluripotent or multipotent stem cells.

BACKGROUND

Pluripotent and multipotent stem cells have the potential to revolutionize various therapeutic applications, especially in the fields of regenerative medicine and pharmaceutical development. One of the obstacles for stem cell-based therapy is the requirement of large number of cells, which can be met by expanding stem cells in a large scale. A number of technical hurdles remain for expansion of such cells using currently available substrates for cell-culture using a bioreactor.

Bioreactors have long been practiced as the preferred scale-up method for cell culture. The use of microcarriers for culturing adherent cells is common in industrial practice, such as in bioprocessing. Typical bioreactor vessels employ some means of agitation, such as internal impellers, rocking or shaking mechanisms to suspend the cells and allow mass transfer of nutrients, oxygen and metabolic waste products. The agitation can subject cells to high degrees of flow-induced stress that can damage cells, especially sensitive ones such as stem cells. A carrier that protects stem cells from agitation-induced damage and provides better stem cell recovery has recently been developed. One of the biggest remaining technological needs is control over stem cell differentiation, both in terms of suppressing spontaneous differentiation as well as enhancing directed differentiation.

Stem cells are inherently susceptible to differentiation based on their local environment, which typically generates the appropriate cell types for the current stage of development or produces cells for generating particular tissues. To control differentiation, the major focus has been on biochemical cues for stem cell growth and differentiation, leading to a great variety of specialized media and surface treatments for the maintenance of stem cell pluripotency or induction of differentiation. Originally, many pluripotent stem cells are grown in a co-culture with mouse embryonic feeder cells (MEF) which conditioned the environment to support pluripotent growth, however this leads to the potential for xeno-contamination and adds to the inherent biological variability of the system. To avoid contamination, a combination of surface treatments with extracellular matrix proteins, different media formulations or other surface-modifiers have been employed to achieve similar results, though the surface coating of extracellular matrix proteins remains a biologically variable source of growth signals for non-recombinant protein mixtures.

Therefore, surface treated cell carriers, which maintain stem cell pluripotency without xeno-contamination, are an unmet need in the art. The development of cell carriers that facilitates stem cell attachment, proliferation and release, while maintaining stem cell pluripotency or directing differentiation under reduced shear forces is highly desired.

BRIEF DESCRIPTION

One embodiment of a carrier for expansion of pluripotent stem cells, comprises a substrate comprising one or more outer surfaces, wherein the one or more outer surfaces are modified with gas plasma treatment, and wherein one or more structured indentations exist on one or more of the outer surfaces, and the carrier has a length at least about 0.2 mm, a width at least about 0.2 mm, and a height in a range from about 0.05 mm to 1.2 mm and each of the structured indentations has a major axis in a range from about 0.1 mm to 0.5 mm, a minor axis in a range from about 0.1 mm to 0.5 mm and a depth in a range from about 0.025 mm to about 0.5 mm.

A carrier for expansion of pluripotent stem cells comprises a substrate comprising one or more outer surfaces modified with one or more of corona discharge treatment, gas plasma treatment, or chemical functionalization; and a coating of biomolecules disposed on one or more of the modified surfaces, wherein one or more structured indentations on one or more of the outer surfaces, and the carrier has a length of at least about 0.2 mm, a width of at least about 0.2 mm, and a height in a range from about 0.05 mm to 1.2 mm and each of the structured indentations has a major axis in a range from about 0.1 mm to 0.5 mm, a minor axis in a range from about 0.1 mm to 0.5 mm and a depth in a range from about 0.025 mm to about 0.5 mm.

An example of a method for expanding pluripotent stem cells comprises providing a carrier for expansion of pluripotent stem cells, comprising: a substrate comprising one or more outer surfaces modified with one or more of corona discharge treatment, gas plasma treatment, coating, or chemical functionalization; and a biomolecular coating disposed on the modified surfaces, wherein one or more structured indentations on one or more of the outer surfaces, wherein the carrier has a length of at least about 0.2 mm, a width of at least about 0.2 mm, and a height in a range from about 0.05 mm to 1.2 mm and each of the structured indentations has a major axis in a range from about 0.1 mm to 0.5 mm, minor axis in a range from about 0.1 mm to 0.5 mm and depth in a range from about 0.025 mm to about 0.5 mm, seeding and expanding the pluripotent stem cells on the carrier.

One example of a method of making carriers for expanding pluripotent stem cells comprises a) providing one or more flat polymer films, b) forming on the flat polymer films, on one or more sides, one or more structured indentations, c) cutting the treated polymer film into a plurality of portions to form carriers; and d) imparting a surface treatment to the carriers comprising one or more of corona discharge treatment, gas plasma treatment, chemical functionalization or coating.

Another example of a method of making comprises a) providing one or more polymer films comprising one or more structured indentations on one or more sides of the films, b) cutting the polymer film into a plurality of portions to form carriers and c) imparting a surface treatment to the carriers comprising one or more of corona discharge treatment, gas plasma treatment, chemical functionalization, coating or combinations thereof.

DRAWINGS

These and other features, aspects, and advantages of the present invention will become better understood when the following detailed description is read with reference to the accompanying drawings in which like characters represent like parts throughout the drawings, wherein:

FIG. 1A is an image of a carrier of the invention comprising a plurality of indentations showing dimensions of the carrier. FIG. 1B is an image of the same carrier showing dimensions of each indentation.

FIG. 2A is an image of a carrier of the invention comprising one indentation on one side of the base. FIG. 2B is an image of a carrier of the invention comprising one indentation each on two opposing sides of the base. FIG. 2C is a scanning electron microscope (SEM) image of a carrier of the invention comprising a plurality of indentations on one side of the base. FIG. 2D is an SEM image of a carrier of the invention comprising a plurality of indentations on both sides of the base.

Figure 5A:
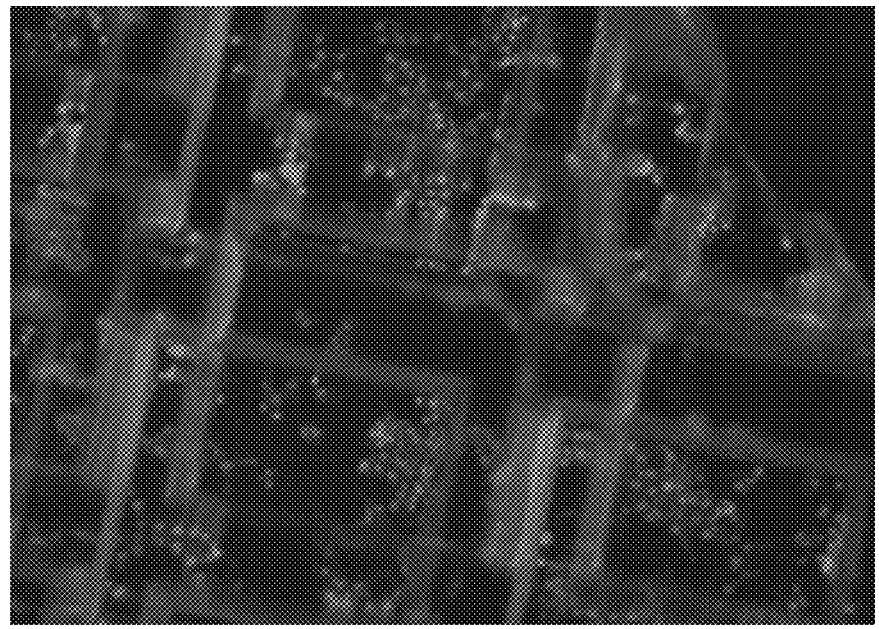
Figure 5B:
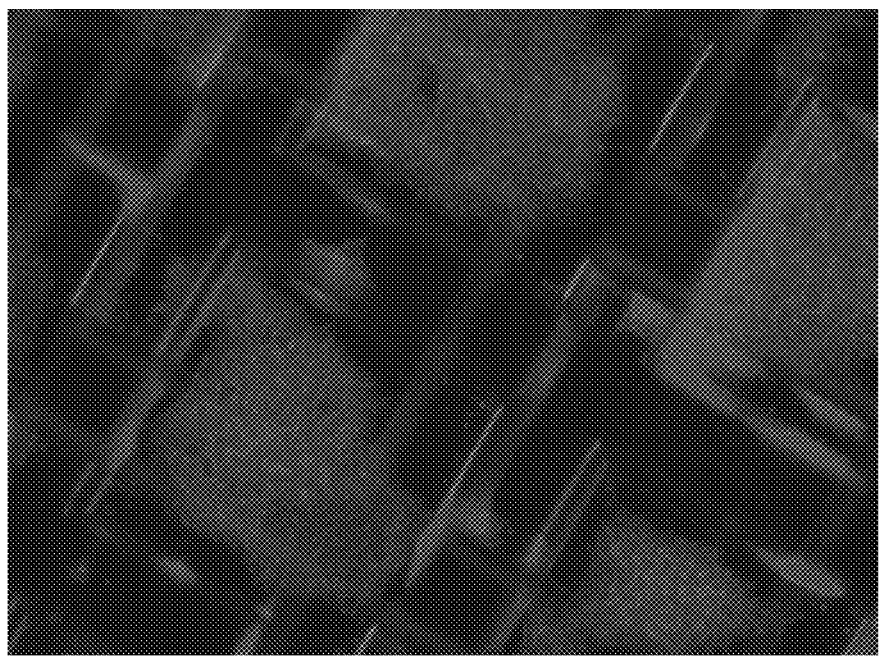
Figure 6A:
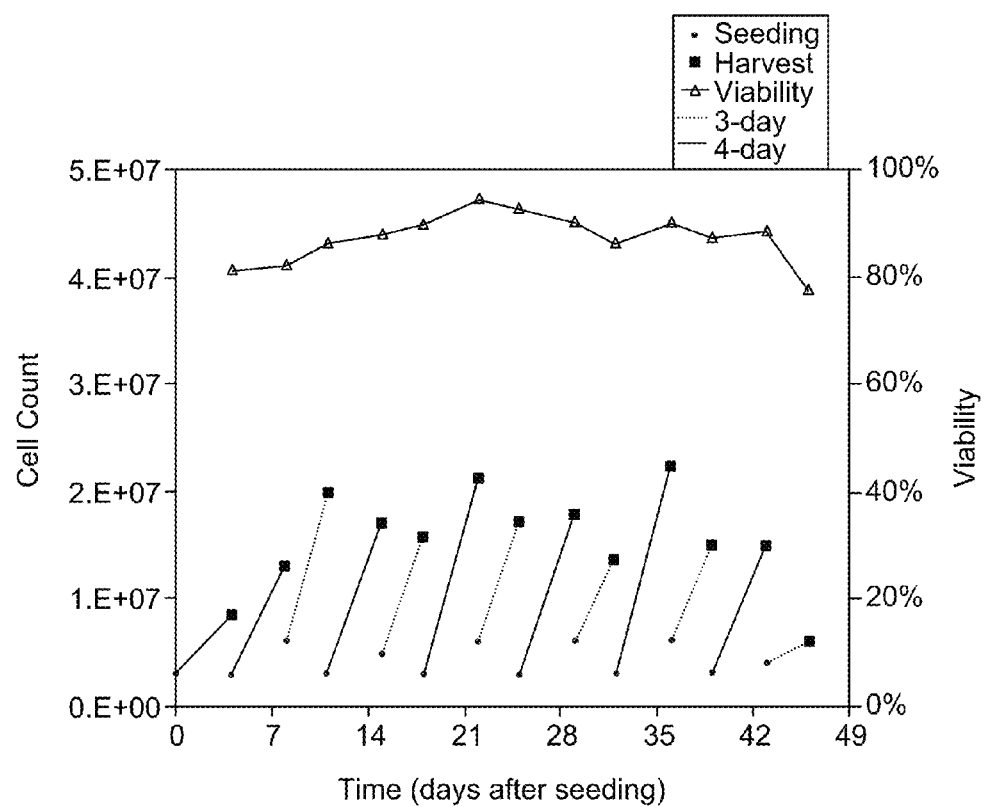
Figure 6B:
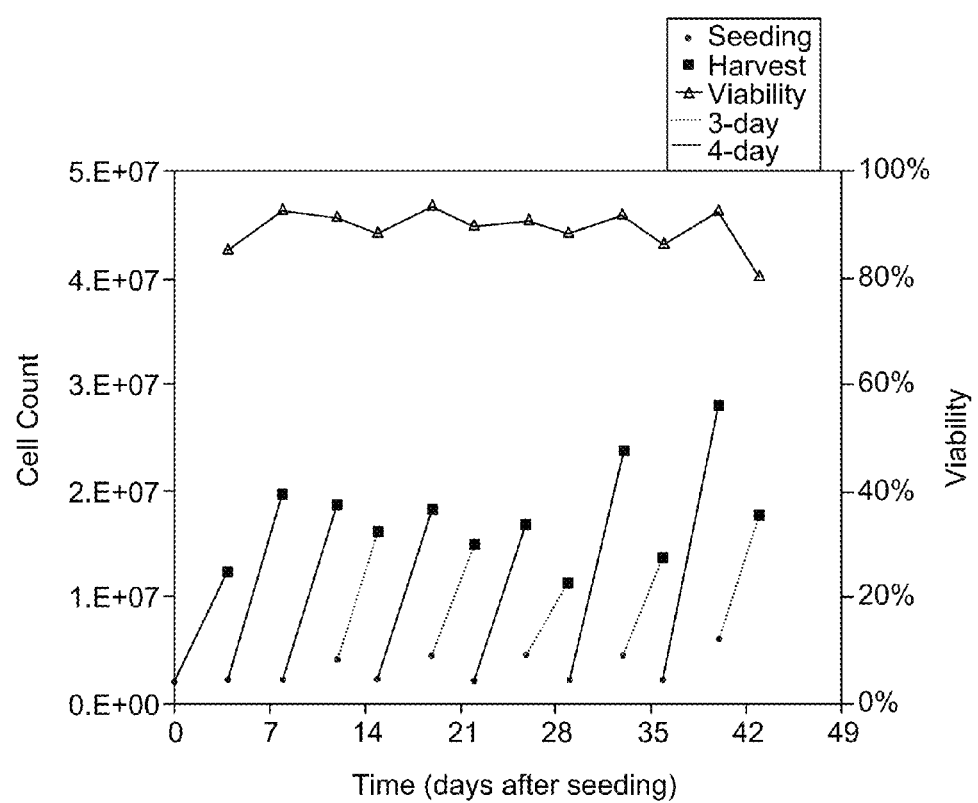
Figure 6C:
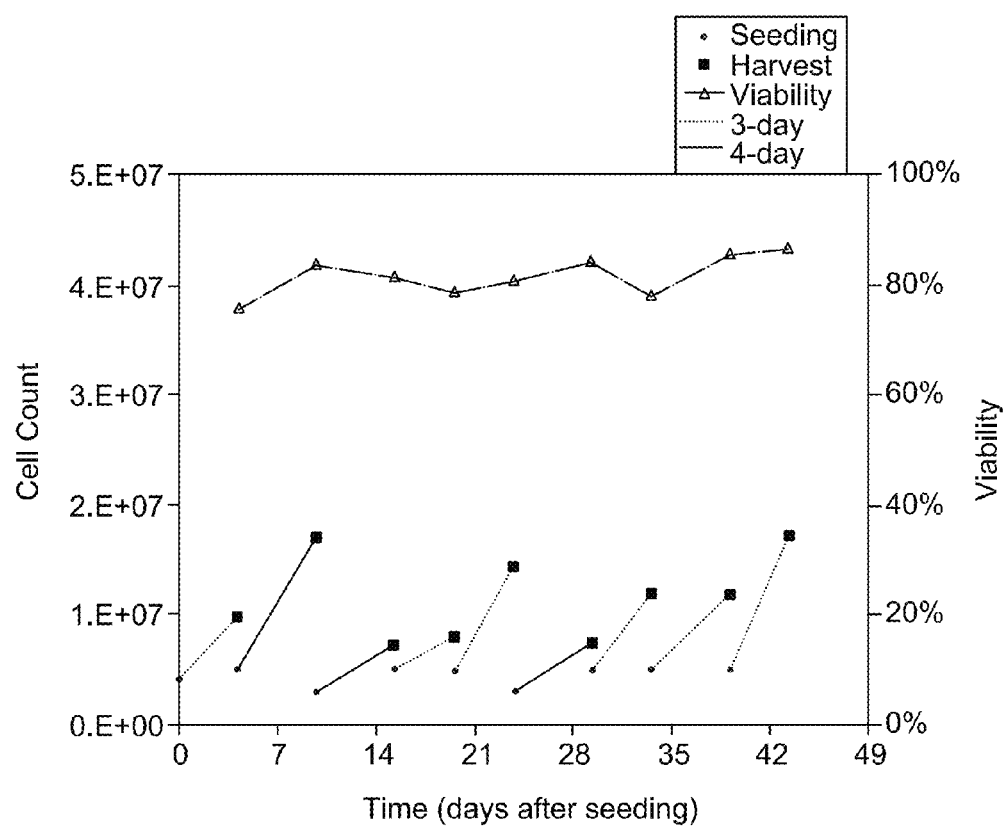
Figure 6D:
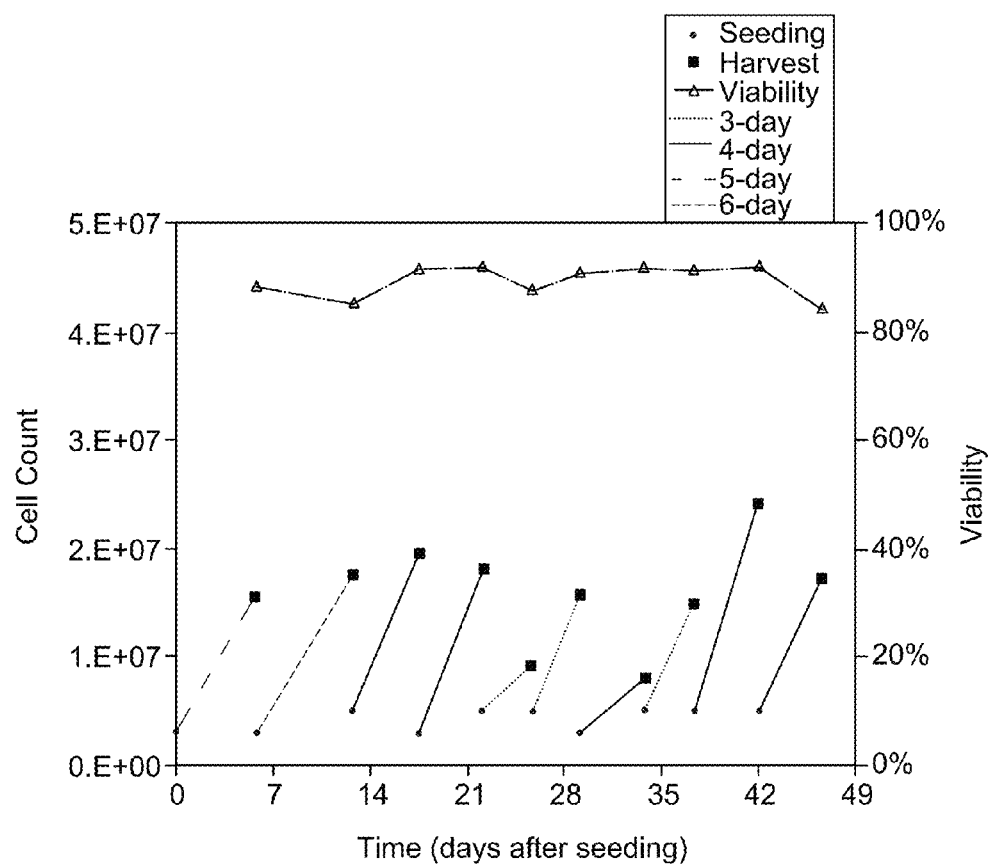
Figure 7A:
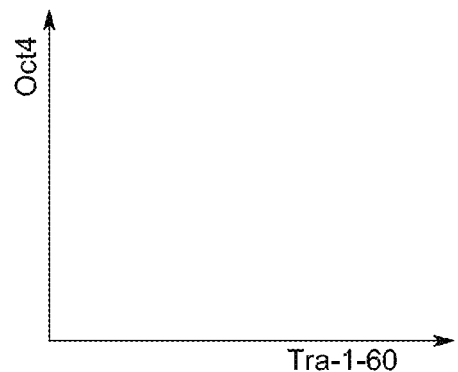
Figure 7B:
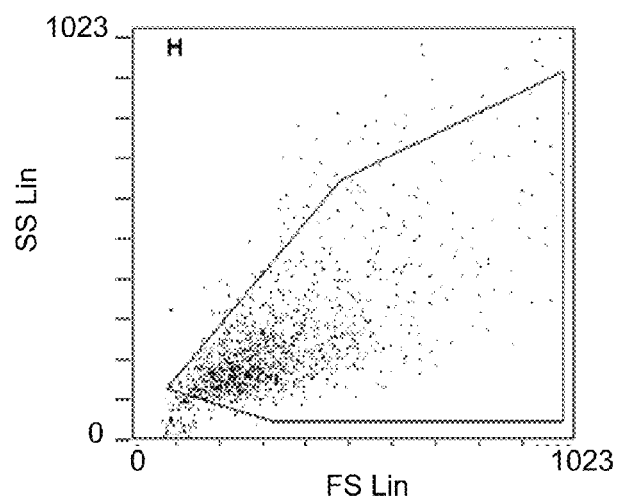
Figure 7C:
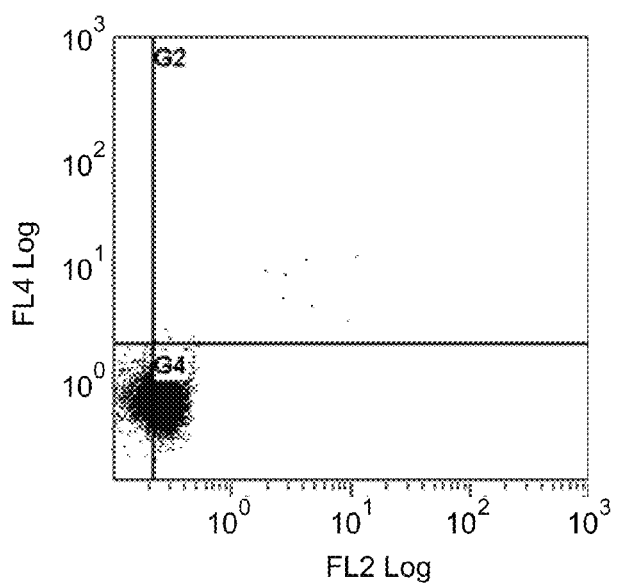
Figure 7D:
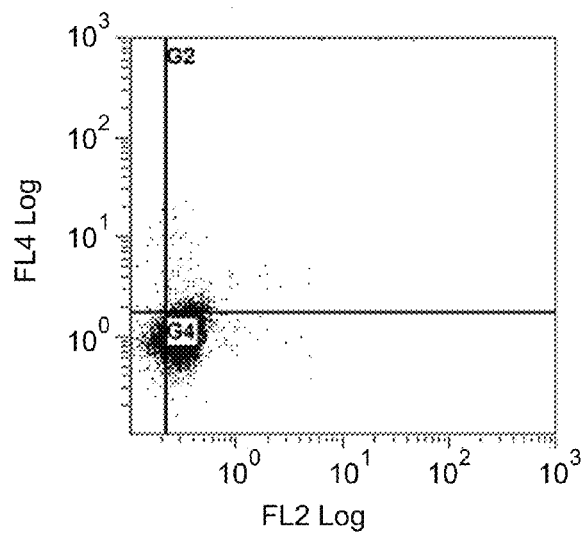
Figure 7E:
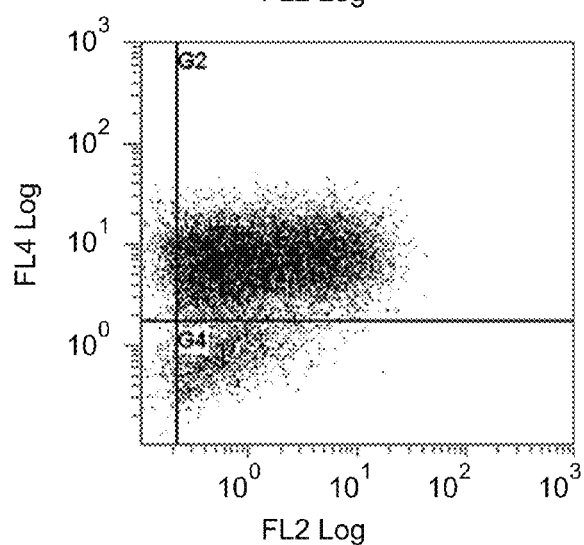
Figure 7F:
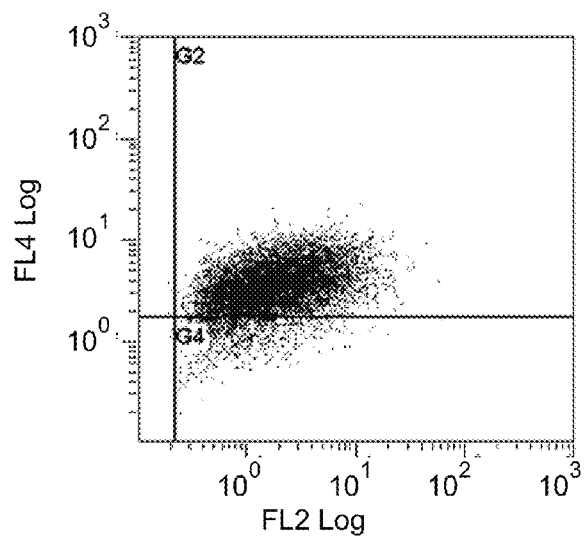
Figure 7G:
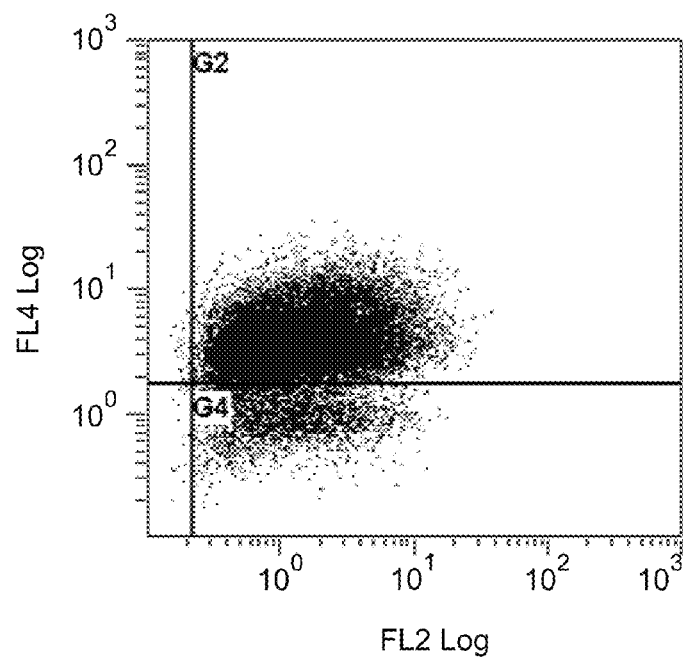
Figure 7H:
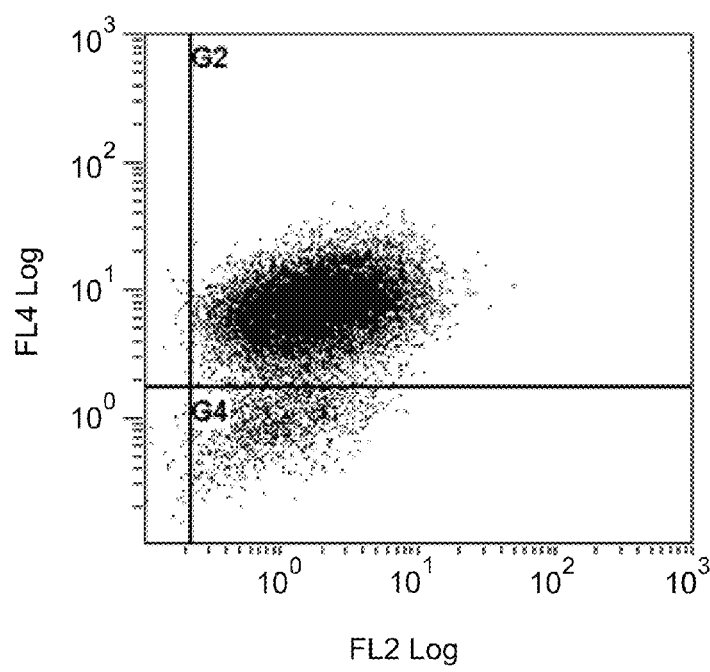

FIGS. 5 A and 5 B are optical microscopy images (40× magnification) of CT2 cells grown on the carriers of the invention in spinner flasks after 4 hours of seeding and after 3 days of seeding, respectively.

FIGS. 6 A, 6 B, 6 C and 6 D represent serial passage expansion of CHB10, CT2, H1 and H7 cells respectively, on the carriers of the invention in the spinner flask.

FIG. 7 A shows a flow cytometric evaluation of the pluripotency markers Oct4 and Tra-1-60 expression on CT2 cells serially passaged on the carriers of the invention in stirred tank reactors. FIG. 7 B shows forward scatter and side scatter properties of the CT2 cells serially passaged on the carriers of the invention in stirred tank reactors using flow cytometric evaluation of the pluripotency markers Oct4 and Tra-1-60. FIG. 7 C is a negative control without staining the cells under the same condition. FIG. 7 D show a flow cytometric evaluation of the pluripotency markers Oct4 and Tra-1-60 expression on CT2 cells staining with isotype antibodies under same condition. FIG. 7 E shows pluripotency marker Oct4 and Tra-1-60 expression in static culture of CT2 cells using flow cytometry. FIG. 7 F shows a flow cytometric evaluation of the Oct4 and Tra-1-60 expression on CT2 cells serially passaged over 2 times on the carriers of the invention in stirred tank reactors. FIG. 7 G shows a flow cytometric evaluation of the Oct4 and Tra-1-60 expression on CT2 cells serially passaged over 10 times on the carriers of the invention in stirred tank reactors. FIG. 7 H shows a flow cytometric evaluation of the Oct4 and Tra-1-60 expression on CT2 cells serially passaged over 19 times on the carriers of the invention in stirred tank reactors.

Figure 8I:
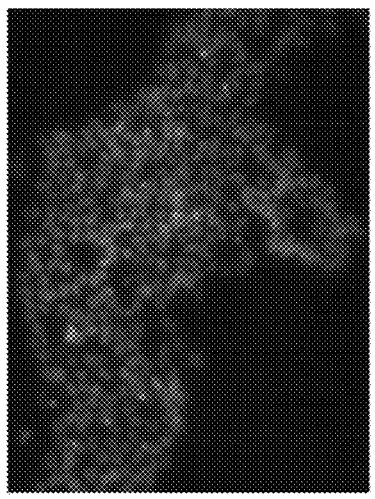
Figure 8H:
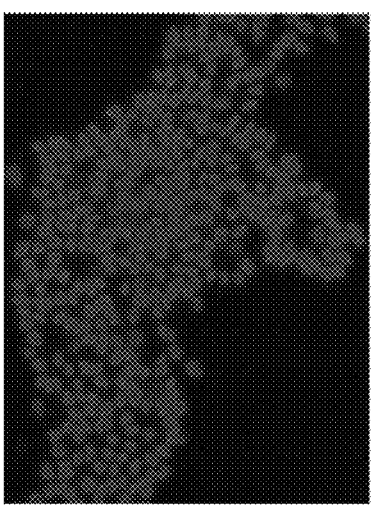
Figure 8G:
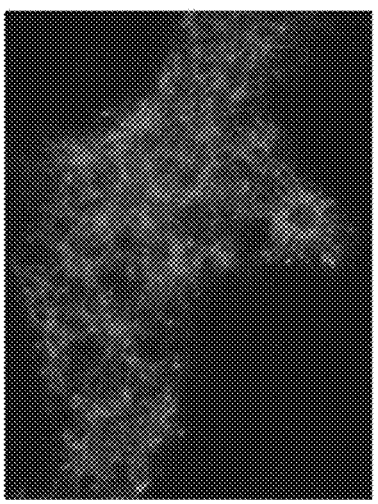

FIGS. 8 A to 8 F represent a series of 100× optical microscopy images of CT2 cells maintained for 10 passages on the carriers of the invention in spinner flasks and FIGS. 8 G to 8 I represent a series of 200× optical microscopy images of CHB10 cells maintained for 22 passages on the carriers of the invention in spinner flasks, where the cells were probed with antibodies against SSEA4 (FIGS. 8 A, 8 D and 8 G), Oct4 (FIGS. 8 B, 8 E and 8 H), and stained with DAPI (FIGS. 8 C, 8 F and 8 I).

FIGS. 9 A, 9 B, 9 C and 9 D represent a series of optical microscopy images of CT2 cells grown on commercial carriers of prototype I, prototype II prototype III and the carriers of the invention respectively, in spinner flasks with 40× magnification.

FIG. 10 A is an optical microscopy image demonstrating human CT2 pluripotent stem expansion on day 2 after cell-seeding on the plasma treated carriers of the invention coated with Matrigel™. FIGS. 10 B, 10 C and 10 D are optical microscopy images demonstrating human CT2 pluripotent stem expansion on non-plasma treated carriers of the invention coated with Matrigel™ in spinner flasks on day 2, day 4 (with 40× magnification) and day 4 (with 100× magnification) after cell-seeding, respectively.

DETAILED DESCRIPTION

One or more of the embodiments of the invention relate to cell carriers for culturing pluripotent or multipotent stem cells, wherein the carriers are suspended in a bioreactor. The carrier may be modified by a surface treatment for better cell attachment, controlled growth and ease of release. The surface treatment may include applying a coating material, gas plasma treatment, corona discharge treatment or combinations thereof.

To more clearly and concisely describe the subject matter of the claimed invention, the following definitions are provided for specific terms, which are used in the following description and the appended claims. Throughout the specification, exemplification of specific terms should be considered as non-limiting examples.

The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Where necessary, ranges have been supplied, and those ranges are inclusive of all sub-ranges there between.

A "carrier" or "carrier for growing cells", as referred to herein, is a support for adhering and culturing cells. The carrier may have indentations on it. Suitable materials of the carrier may include, but are not limited to, polymers, copolymers or blends of polymers. The carrier may further be coated with a suitable coating material for effective cell adherence and proliferation. The carrier may have one or more surface treatments, such as gas plasma treatment.

A "major axis", as referred to herein, is the longest dimension of each indentation present on the carrier surface. For example, for a rectangular indentation, length of the indentation is referred as the 'major axis'. A "minor axis", as referred to herein, refers to a dimension other than the longest dimension, of each indentation present on the carrier surface. For example, for a rectangular indentation, width of the indentation is referred as the 'minor axis'. For example, the major axis is the same as the minor axis for a square indentation as the length and width are same, as shown in FIGS. 1B, 14, and 16 respectively, the major axis is a diameter for a circular indentation as shown in FIG. 2B, 14, major axis is length for a rectangular indentation, and major axis is the major axis of an elliptical indentation.

An "aspect ratio", as referred to herein, is a ratio of depth to major axis of each structured indentation. For example, an aspect ratio for a circular indentation is a ratio of depth to diameter.

A "biomolecular coating", as referred to herein, is a coating comprising molecules either derived from biological system or synthetically made. The biomolecular coating may comprise biological proteins, recombinant proteins, natural peptides, synthetic peptides, oligomers, nucleic acids, or carbohydrates.

Embodiments of the carrier in suspension comprise one or more outer surfaces; wherein one or more of the outer surfaces of the carrier comprise one or more structured indentations and the surfaces are sometimes modified with gas plasma treatment to enhance cytophilicity. The invention also comprises methods of making the carrier, and methods and kits for culturing cells using the carriers for cell growth.

One or more embodiments of a carrier for expansion of pluripotent stem cells comprise a substrate comprising one or more outer surfaces where the surfaces are modified with gas plasma treatment. The substrate further comprises one or more structured indentations on one or more of the outer surfaces, where the carrier has a length of at least about 0.2 mm, a width of at least about 0.2 mm, and a height in a range from about 0.05 mm to 1.2 mm and each of the structured indentations has a major axis in a range from about 0.1 mm to 0.5 mm, a minor axis in a range from about 0.1 mm to 0.5 mm and a depth in a range from about 0.025 mm to about 0.5 mm.

Figure 1A:
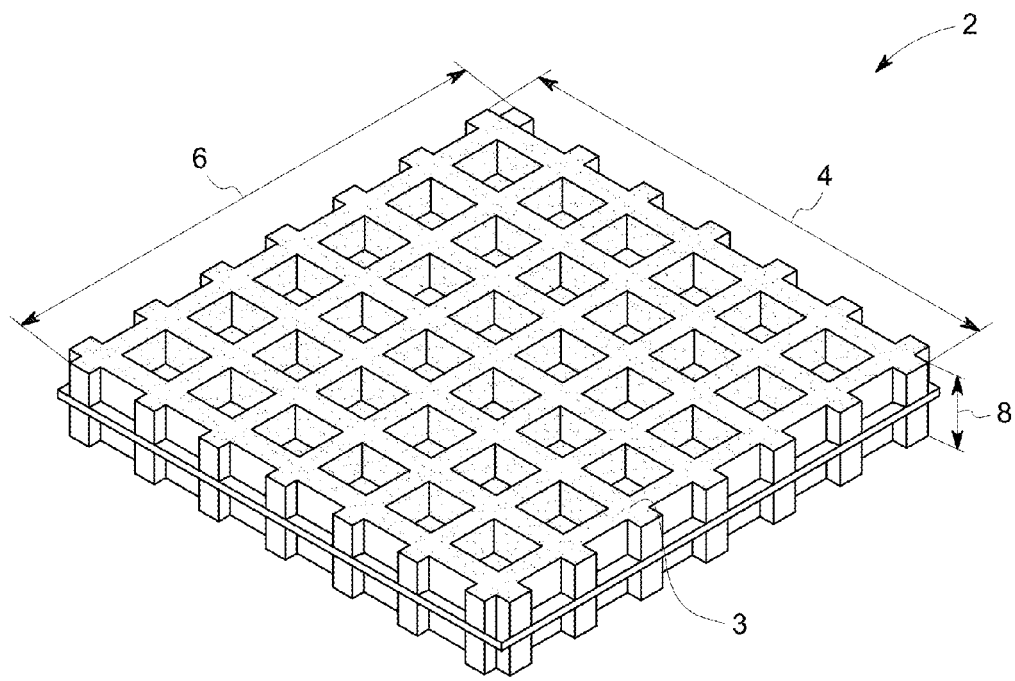
Figure 1B:
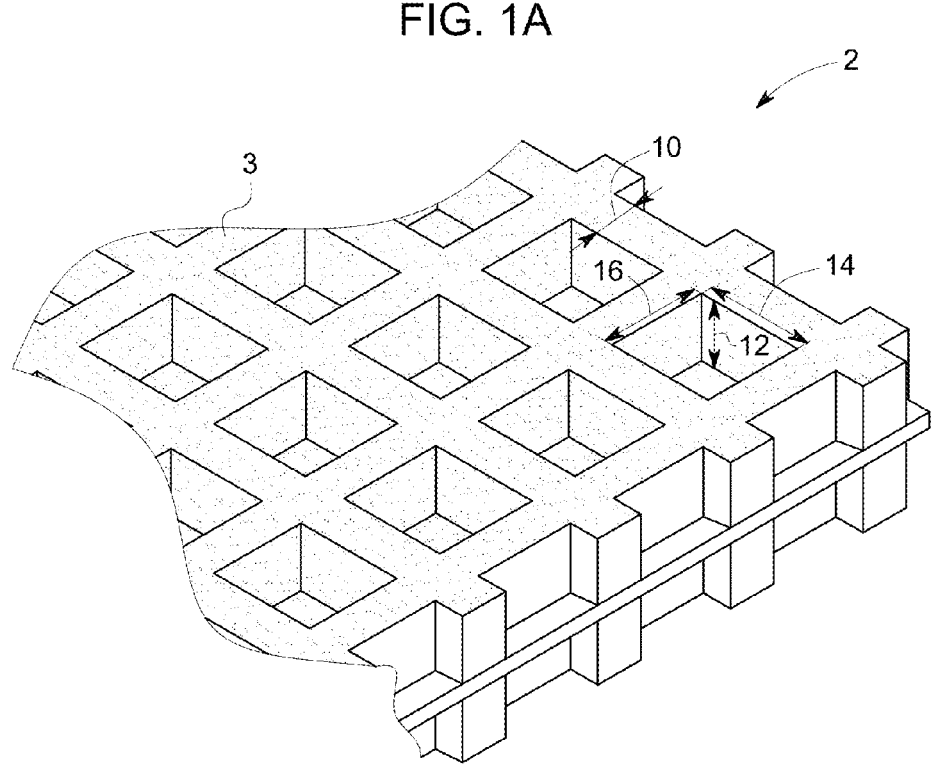

As noted, the carrier for growing adherent cells comprises one or more outer surfaces; and one or more structured indentations in one or more of the outer surfaces, wherein the carrier 2, as shown in FIG. 1A, has a length 4 of at least about 0.2 mm, a width 6 of at least about 0.2 mm, and a height 8 in a range from about 0.05 mm to 1.2 mm. In some embodiments, the carrier has a length 4 in a range from about 0.2 mm to 7 mm, a width 6 in a range from about 0.2 mm to 7 mm, and a height 8 in a range from about 0.05 mm to 1.2 mm. In some embodiments, the carrier has a width and length from about 0.2 to 25 mm. In some embodiments, the wall-thickness 10 of the carrier is in a range from about 0.05 mm to 2 mm. In some embodiments, the carrier comprises a surface 3, wherein the surface is treated with one or more of corona discharge treatment, gas plasma treatment, chemical functionalization or coating.

Embodiments of the structured indentations, as shown in FIG. 1B, comprise a depth 12, a major axis 14, and a minor axis 16, wherein the major axis 14 of an indentation is in a range from about 0.1 mm to 0.5 mm, the minor axis 16 is in a range from about 0.1 mm to 0.5 mm, and the depth 12 is in a range from about 0.025 mm to about 0.5 mm. The wall-thickness 10 is in a range from about 0.05 mm to 2 mm. As used herein the term, 'depth' of an indentation refers to the depth of the inner wall of each indentation. As used herein, the term 'wall-thickness' refers to a thickness of a single wall for a carrier with single indentation, or thickness of each of the multiple walls for the carrier with a plurality of structured indentations as shown in FIG. 1B. Each of the structured indentations has an aspect ratio in a range from about 0.1 to about 1.5. In some embodiments, the carrier comprises a surface 3, wherein the surface is treated with one or more of corona discharge treatment, gas plasma treatment, chemical functionalization or coating.

Figure 2A:
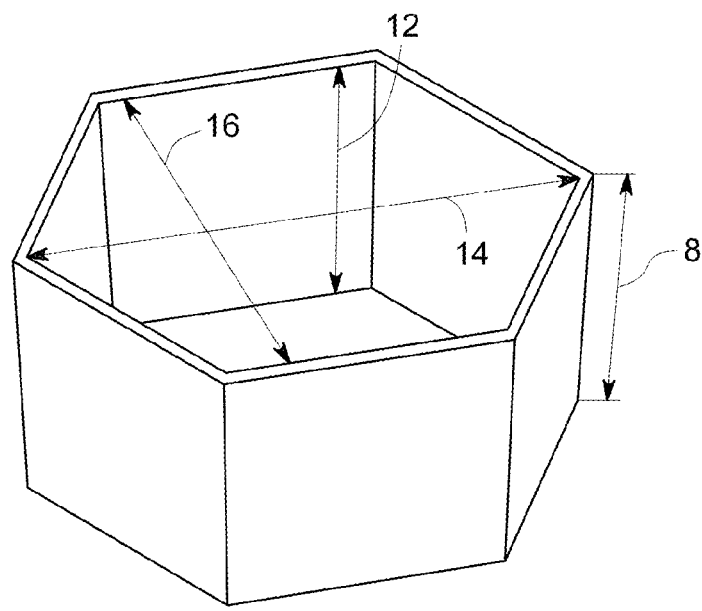
Figure 2B:
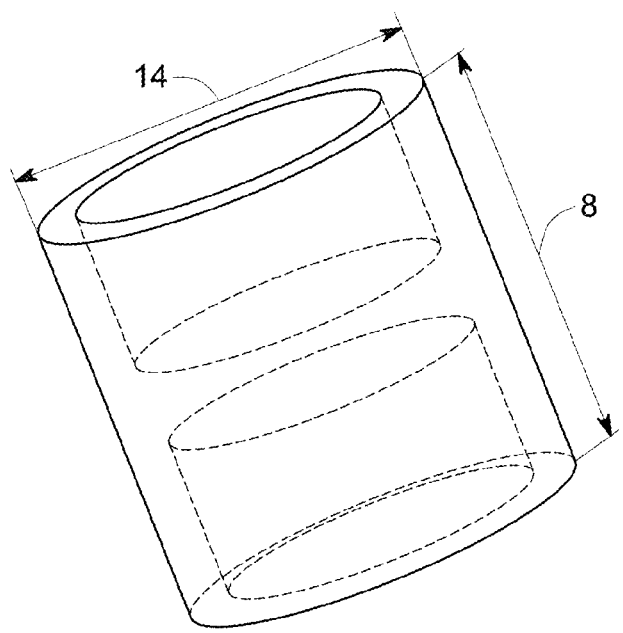

In one embodiment, the carrier may comprise one indentation on at least one surface of the carrier as shown in FIG. 2A. In this embodiment, the carrier is a 'cup' like structure on one outer surface of the base with a continuous wall surrounding the base of the carrier. In an alternate embodiment, the carrier may comprise one indentation on each of the surfaces of the carrier as shown in FIG. 2B. In this embodiment, the carrier has two 'cup' like structures on opposing outer surfaces of the base with a continuous wall surrounding the cups. This carrier may be useful for specific cell culture conditions or for specific cell-types. The single carrier (FIGS. 2A and 2B) has a length in a range from about 0.1 mm to 6.5 mm, a width in a range from about 0.1 to 6.5 mm, and a height 8 in a range from about 1 mm to 10 mm, and a wall-thickness 10 of the carrier in a range from about 0.05 mm to 2 mm. In case of a single 'cup' (FIG. 2A) or two 'cups' on opposing sides of the base (FIG. 2B), has a length that is same as the major axis 14 as shown in FIGS. 2A and 2B, a width that is same as the minor axis 16, and the cup has a depth 12, as shown in FIG. 2A.

Figure 2C:
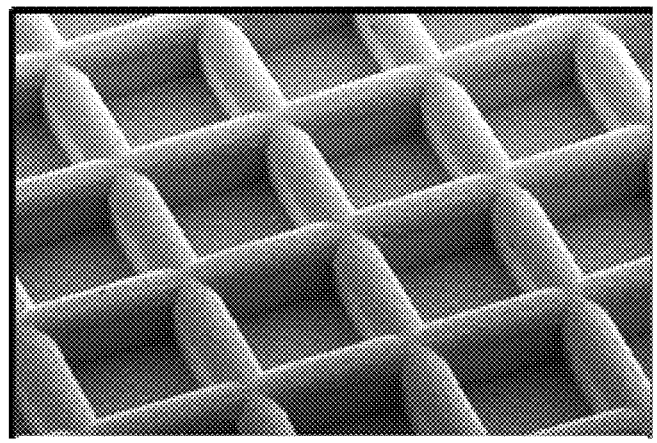
Figure 2D:
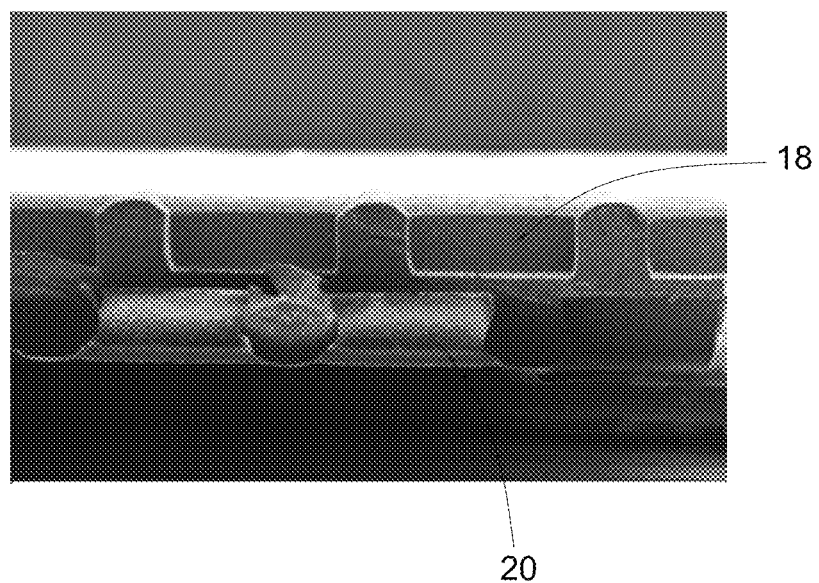

In some embodiments, the carrier comprises at least one surface for growing adherent cells, wherein more than one structured indentation is present on the surface, for example, the carrier has a plurality of structured indentations on one outer surface of the base, as shown an SEM image in FIG. 2C. The carrier, in one embodiment, comprises at least two outer surfaces. In this embodiment, more than one structured indentation is formed on each of the outer surfaces, such as 18 and 20 are the structured indentations on the upper and lower surface respectively, as shown in FIG. 2D. In this embodiment, the carrier has a plurality of indentations on opposing outer surfaces of the base (FIG. 2D).

In some embodiments, the carrier has a substantially planar disc-like structure. As used herein, 'substantially planar disc', refers to a disc, which provides a planar surface area for growing cells. The shape of the carrier may be polygonal. In one or more embodiments, the shape of the carrier may vary, for example, the carrier may have an overall perimeter that is circular, elliptical, triangular, rectangular, square, pentagonal, or hexagonal shape.

The disc like-structure of the carrier may provide higher surface area per unit volume for culturing cells, relative to, e.g. spherical structures. The shape and size of the carrier may also allow about 2 to 50-fold of hESC expansion per passage. Efficient separation of enzymatically (e.g. release using trypsin or accutase, etc.) or chemically released (EDTA, Cell Dissociation Buffer)) cells from the carriers is facilitated due to the significant size difference between the cells (~15 micron) and the carriers (larger than 0.2 mm). Released cells may be separated from the carriers via simple filtration, or separation of the supernatant after allowing the carriers to settle.

The structured indentation has a wall that protrudes normal to the outer surface of the carrier, as shown in FIGS. 1A, 1B, 2A, and 2B. The wall height is chosen to balance the various requirements of the carrier, for example, a lower wall (i.e. shallow indentation) allows higher packing density of carriers per unit volume, and therefore can provide higher cell yield per unit volume of reactor. Moreover, transport of oxygen, nutrients and metabolic waste to/from the cells is facilitated at lower wall height (i.e. shallower indentations). However, a higher wall (i.e. deeper indentation) can offer higher degrees of protection from hydrodynamic forces arising due to agitation inside the bioreactor. Further, a higher wall or deeper indentation can provide a microenvironment that prevents dilution of any cell-secreted molecules. This may be advantageous if cell-cell signaling or autocrine factors are a desired part of the cell culture or processing operations. The desired range of the height of the wall projected above the plane of the carrier is therefore optimized with these factors in mind, in a range from 0.05 mm to 1.2 mm; in some embodiments from about 0.05 mm to about 0.5 mm, or in some embodiments, from about 0.08 mm to about 0.2 mm.

In use, the carriers are maintained in suspension inside a bioreactor, comprising a fluid having a convective motion that generates sufficient transport of nutrients and oxygen to cells. The cells adhere to the surface of the structured indentations having a flat or curved wall of sufficient height such that the effect of fluid-induced hydrodynamic stress on the cells is minimized. The carrier comprises an optimum depth of indentations, balancing the needs of the adherent cells providing access to nutrients and metabolites, while protecting the cells from exposure to hydrodynamic shear generated by fluid motion.

Unlike other adherent cells, the pluripotent stem cells, such as hESCs may adhere poorly to a polymeric surface due to cell phenotype or culture conditions. A surface treatment can be employed to improve the cell attachment and limit spontaneous differentiation. The surface treatment may include plasma treatment, coatings, surface functionalizations or combinations thereof. The plasma treated surface may result in faster and more robust cell attachment on the cell carriers and result in higher cell yields compared to un-treated carriers.

As noted, the one or more surfaces of the carriers may be modified with plasma treatment. Plasma treatment may result in increasing hydrophobicity or hydrophilicity. In some embodiments, the polymer-based carrier surfaces are further modified with functional groups or coatings to enable better cell attachment and growth. Plasma treatments may be broadly categorized into two types: atmospheric plasma treatment in which an electrical energy source is combined with atmospheric gases to create a reactive plasma, known as corona discharge treatment. The other treatment comprises vacuum plasma treatment wherein an electrical or a radio frequency energy source is used in combination with a vacuum chamber containing pressurized gases including oxygen, nitrogen, nitrous oxide, carbon monoxide, carbon dioxide, argon or combinations thereof to create a reactive plasma. In some embodiments, a surface treatment is imparted to the embossed polymer film comprising one or more of corona discharge treatment, gas plasma treatment, chemical functionalization, coating or combinations thereof.

In one or more embodiments, the surface modification may be achieved via plasma treatment. The plasma treatment on each of the surfaces may modify the surface property of the carriers, e.g. hydrophobicity, hydrophilicity or wettability. Wettability may be quantified by contact angle measurements. The increased hydrophilicity of plasma treated carriers is known to improve cell attachment and growth compared to growth on untreated polymer surfaces. In some embodiments, the plasma treatment may comprise gas plasma treatment. The gas plasma treatment may impart surface chemistry through the introduction of oxygen, nitrogen, carbon dioxide, nitrous oxide, ammonia or combinations thereof. In some embodiments, the polystyrene films are plasma treated with two pure gases such as oxygen and ammonia, either sequentially, or as a gas mixture of oxygen and ammonia. The plasma treatment typically increases the oxygen content of the surface, introducing hydrophilic ketone, carboxylate and hydroxide moieties on the surface. The modified surface chemistry may help in adsorption of extracellular matrix proteins (ECM) such as fibronectin, fibrinogen, vitronectin, laminin, etc., which enhances cell attachment and cell proliferation on the treated surface.

One index of hydrophobicity or hydrophilicity is the contact angle of a water droplet on the surface. Contact angle can be measured by techniques well-known in the art. For example, a measurement of the water contact angle formed on a flat polystyrene film is proportional to the degree of hydrophilicity imparted by the plasma treatment. In one or more embodiments, the water contact angle for the plasma treated carrier surface may be in a range from about 10° to about 90°. In some embodiments, the water contact angle for the plasma treated carrier surface is from 30° to 70°. The water contact angle increases over time after plasma treatment due to surface chemistry reorganization to an equilibrium state. The plasma treatment further provides a surface chemistry with long-term stability.

In some embodiments, the plasma treatment may be carried out in a plasma reactor. The plasma reactor may be a vacuum vessel with a gas at low pressure, typically 10 to 1000 mTorr. When a high frequency electric field is generated in the reactor, plasma is formed containing reactive species like ions, free radicals and vacuum-UV photons. These species may react with the polymer surface and may cause chemical modifications accompanying with corresponding changes in various properties, which depend on the nature of the gas and the plasma parameters. Gases such as oxygen, ammonia and argon are typically used for modification of the polymer surfaces. In some embodiments, carbon dioxide, ammonia or nitrogen is used for plasma treatment. In one embodiment, the polymer surface is modified by oxygen-plasma treatment to increase the cytophilicity of the surface. The surface functionality may also be altered via wet chemical methods such as oxidation treatments using perchloric acid or permanganate or partial hydrolysis using strong acids or bases.

In addition to gas type, the plasma system has different factors, such as process settings that can be varied. In one or more embodiments, the factors include chamber pressure, device power (50-2000 W), duration, gas flow rate and plasma mode. The chamber pressure, device power, duration and gas flow rate are continuous factors, which are maintained during the whole procedure. The plasma mode in some systems may be set to either reactive ion etch (RIE) or plasma etch (PE) mode, with the reactive ion etch mode as one of the desired mode in these embodiments.

In some embodiments, the surfaces are treated with corona discharge to modify one or more surface properties of the carriers. In corona discharge treatment, a current develops from an electrode with a high potential in a neutral gas, such as air. Ionization of the gas generates a layer of plasma around the electrode. The ions generated eventually pass the charge to nearby areas of lower potential, or recombine to form neutral gas molecules. Surfaces of organic films such as polystyrene, polyesters and others may be oxidized when exposed for a short time to the reactive air plasma generated by corona discharge. Corona discharge treatment can increase the oxygen content on the polymer surface and improve the film wettability by water.

Generally, mouse or human fibroblast feeder cell layers, defined as serum-free medium or conditioned media have been used for culturing hESCs and iPSCs. The embodiments of the carriers may comprise a coating that provides a xeno-free alternative to feeder cell layers which reduces the probability of contamination. The present embodiments of the carriers provide feeder-free, and in some embodiments chemically defined coatings, which are useful for culturing cells that may safely be used for therapeutic applications.

A variety of biomolecular coatings may be used to modify the carrier surfaces to enhance cell attachment. In some embodiments, the carriers further comprise biomolecular coatings, such as proteins or peptides on the plasma treated carriers. In these embodiments, the biomolecular coating is disposed on the plasma treated surface to further increase cytophilicity. In some other embodiments, the non-plasma treated carriers are coated with biomolecular coatings. In these embodiments, the biomolecular coatings are disposed directly on the carrier surface.

One or more embodiments of the carrier comprise biomolecular coatings that comprise biologically derived proteins or peptides, recombinant proteins or synthetic peptides. In one embodiment, the coating comprises extracellular matrix (ECM) proteins, proteoglycans, factors derived from a mouse sarcoma cell line or combinations thereof. In some embodiments, the biologically derived proteins may include various structural proteins such as collagen, laminin, entactin, vitronectin or fibronectin. In some embodiments, the coating comprises recombinant proteins. The recombinant proteins may include laminin 511 or laminin 521. In one embodiment, the surfaces are modified with recombinant fibronectin to enhance surface cytophilicity for better attachment of the cells. In some embodiments, cells are attached to extracellular matrix (ECM) through integrin, which is cell adhesion receptor that supports cell proliferation and differentiation. Integrin can bind to ECM proteins, such as collagen, fibronectin, vitronectin, laminin and N-linked glycoproteins.

The coating may further comprise natural polypeptides or synthetic polypeptides. In one or more embodiments, the coating further comprises growth factors that promote differentiation or proliferation of pluripotent or multipotent cell types. The coated surfaces support adhesion and expansion of stem cells in their undifferentiated state or directed differentiation into specialized cell types. One or more embodiments of the coating may comprise growth factors such as bFGF, TGF β1, Human Insulin, Human Holo-Trasferrin, Human Serum Albumin, Glutathione or combinations thereof. In some embodiments, the synthetic peptide comprises the RGD sequence. Most of the ECM proteins include RGD peptide sequences and the cells can be attached through RGD binding via integrin to provide undifferentiated proliferation of hESCs in serum-free media.

The plasma treated carriers are compatible with coatings used for hESC, such as, Matrigel™, recombinant proteins such as Laminin521, or synthetic substrates such as Synthemax® II. In one embodiment, the coating comprises Matrigel™, which is used as an attachment substrate for culturing embryonic stem cells. In the absence of feeder cells, the embryonic stem cells are grown using Matrigel™, which comprises extracellular matrix components derived from a mouse sarcoma cell line (Engelbreth-Holm-Swarm) extracellular matrix material. The Matrigel™ is heterogeneous in composition containing different structural proteins including laminin, entactin and collagen with adhesive peptide sequences. Matrigel™ contains numerous other proteins in different amounts and its exact composition may vary. In another example, the coating material for culturing hESC may include Laminin521 or Synthemax® II. The coated carriers are compatible with gamma sterilization.

The carrier surface may be modified, for example, to enhance cell release as well as cell attachment. The coating may be made, for example, of a thermoresponsive polymer, pH responsive polymer, or combination thereof. Thermoresponsive polymers may include, but are not limited to, poly (N-isopropylacrylamide) (PNIPAM), poly(di(ethyleneglycol)methylether methacrylate) (PDEGMA). pH responsive polymers may include, but are not limited to, copolymers of acrylic acid, dimethylaminoethylacrylate, and hydroxyethylacrylate. The coating may comprise one or more layers. In some embodiments, where the coating comprises multiple layers, the layers may be homogeneous or heterogeneous. For one example, one layer may be made of thermoresponsive polymer, and another layer may be made of pH responsive polymer. Thermoresponsive or pH responsive polymer coatings on the surface can facilitate easy release of cultured cells from the carrier surface.

Figure 9B:
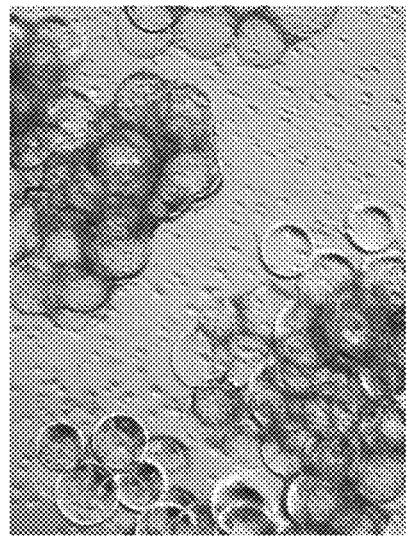
Figure 9D:
Figure 9A:
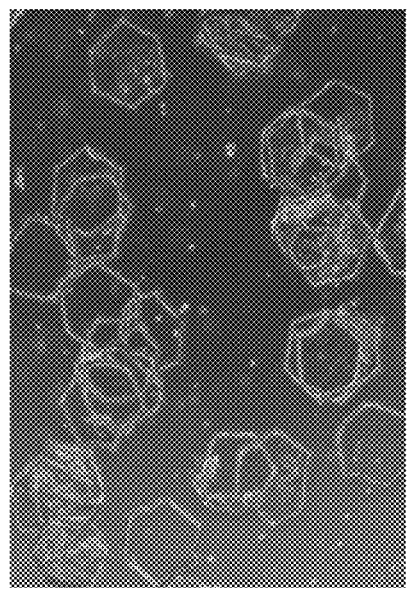
Figure 9C:
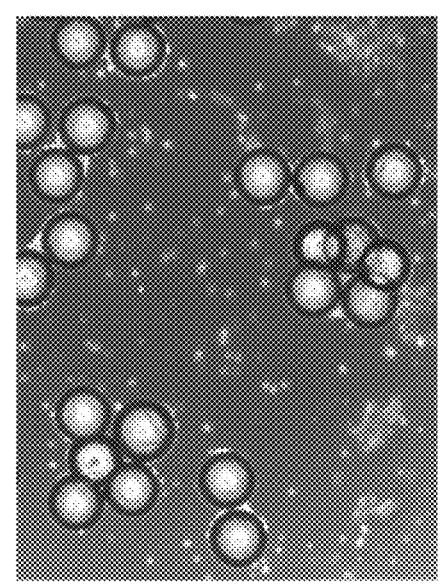
Figure 10A:
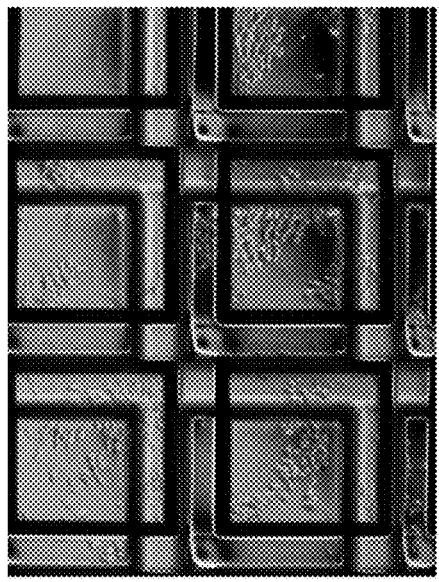
Figure 10B:
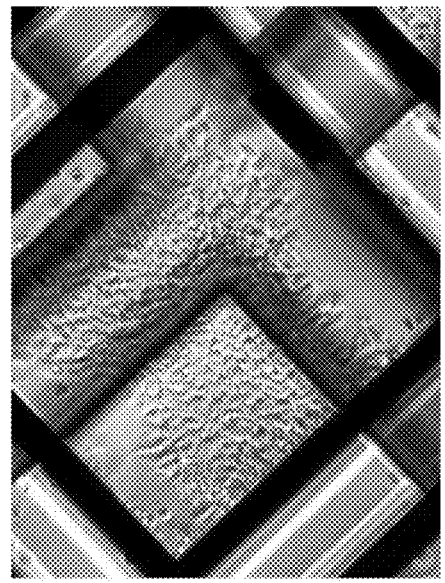
Figure 10C:
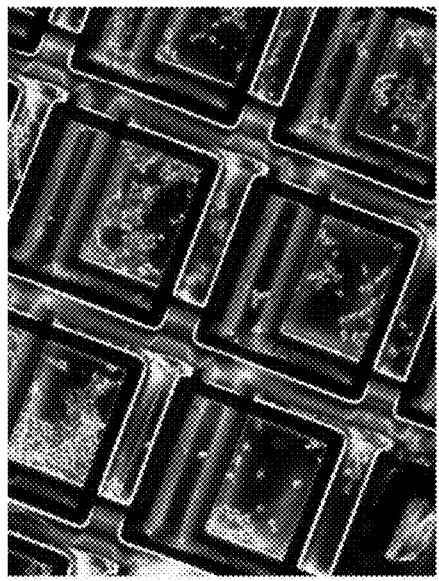
Figure 10D:
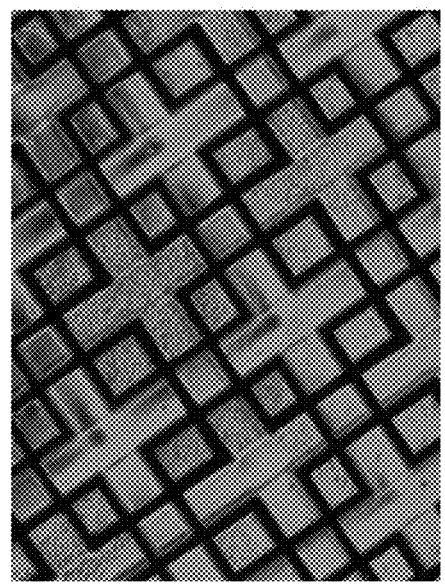

The structured indentations may also form relief features on the carrier surface. The relief feature may be present on one or more surfaces of the carriers, which prevents the carriers from sticking to each other. Carrier sticking or clumping has been seen to be an issue with certain types of flat or smooth carriers during low shear mixing, as shown in FIGS. 9A, B and C. The relief features on the carrier also serve to prevent the carriers from sticking to the inner walls of the reactor or culture vessel, which facilitates cleaning the reactors/culture vessels between batches of cell culture.

A cross sectional profile of each indentation may have, as non-limiting examples, a polygonal, a circular, or an elliptical shape. Each of the polygonal indentations may have, as non-limiting examples, a triangular, rectangular, square, pentagonal or hexagonal shape. The dimension of the major axis and minor axis of the indentations may be the same or different.

The carrier may be made of glass, polymer, ceramic, metal or a combination thereof. In one embodiment, the carrier is made of a polymer or a copolymer or a blend of polymers. The polymers may comprise, but are not limited to synthetic and natural polymers such as, polyester including polyethylene terephthalate (PET), polystyrene, polycarbonate, polyamide, polyurethane, olefin polymer, dextran, silicone, or polyacrylate, polymethacrylate or copolymer or blend of polymers thereof. In one specific embodiment, the carrier is made of polystyrene.

The polymer may be transparent, which allows cell observation under an optical microscope. In certain embodiments, the carrier has a substantially planar disc shape, which facilitates cell visualization by preventing lensing effects. Refraction of light can be a hindrance to visualization of cells on spherical carriers of certain refractive index. Cell visualization is useful, for example, for culturing and monitoring cells during stem cell expansion. In some embodiments, the polymer and surface treatment is substantially free of components of animal origin. This is especially beneficial in therapeutic applications, e.g. in the production of cells for cellular therapies. The polymer may be rigid at room temperature or cell culture temperature, non-porous and may have non-swelling properties in water, PBS or growth medium. The rigid, non-swelling, non-porous properties of the polymer can facilitate cell release, for example, when using standard enzymatic release protocols.

An example of a method of making a carrier for growing cells, comprises providing a plurality of flat films and laminating the flat films to form a solid support. The solid support is subjected, to a method such as embossing, casting thermoforming, or injection molding to form structured indentations. In some embodiments, the solid support is embossed to form an embossed solid support, and the embossed solid support is cut into a plurality of portions or pieces to form a plurality of carriers. The plurality of embossed carriers is further treated with plasma to form plasma treated embossed carriers. In some other embodiments, the solid support is embossed to form structured indentations and make an embossed solid support, which is further treated with a plasma to form a plasma treated embossed solid support, followed by cutting or dicing the plasma treated embossed solid support to a plurality of portions or pieces to form a plurality of carriers. In one example, the embossing of the solid support is performed using a mold.

Figure 3:
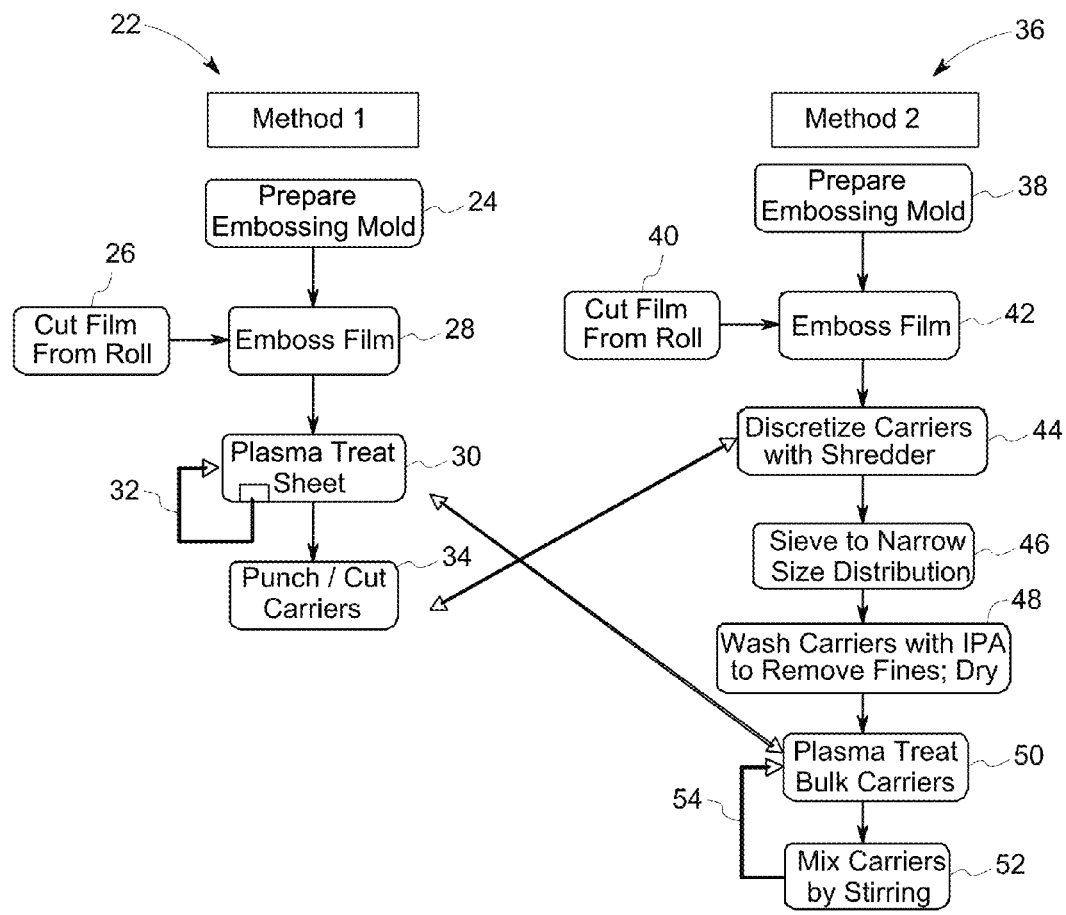
FIG. 3 is a process flow diagram of an example of methods of making carriers of the invention on a small scale in batch mode.

In one example, a process for making a carrier for growing cells is generally illustrated in FIG. 3. The process comprises two alternate methods, method (1) and method (2). The method (1) 22 comprises the steps of preparing embossing mold 24, and cutting a film from a roll 26, followed by embossing the film 28. The embossed film is then treated with plasma 30 to form plasma treated embossed solid support. In some embodiments, the embossed film is optionally plasma treated on the other side of the film for better uniformity of treatment 32. The plasma treated embossed film is then diced or otherwise discretized into a plurality of carriers 34.

The method (2) also may comprise a method 36 comprising the steps of preparing embossed mold 38, and cutting a film from a roll 40, followed by embossing the film 42. In some embodiments, the embossed film is obtained from a source and then the film is processed to cut the films into small pieces. The embossed film is cut or diced or otherwise discretized to generate embossed pieces 44, which can then be sieved to a narrow size distribution 46. In some embodiments, the carriers are then washed with a wash fluid such as water or a mixture of water and alcohol to remove fine particles, followed by drying 48. The carriers are then subjected to a plasma treatment 50 in bulk accompanied by mixing to ensure uniformity of surface treatment 52 to form plasma treated embossed carriers. The plasma treated carriers are then washed with a wash fluid such as water or a mixture of water and alcohol to remove fine particles. The methods (1) and (2) (as described above 22 and 36) can be modified to produce carriers on large scale using roll-to-roll operations for some or all of the steps of manufacturing. For example, the embossing or structure generation step can be scaled-up into a roll-to-roll operation, and the plasma treatment operation can be done in bulk in drum-style treaters, and the discretization can be done via roll-to-roll or sheet-fed cutting operations.

Figure 4:
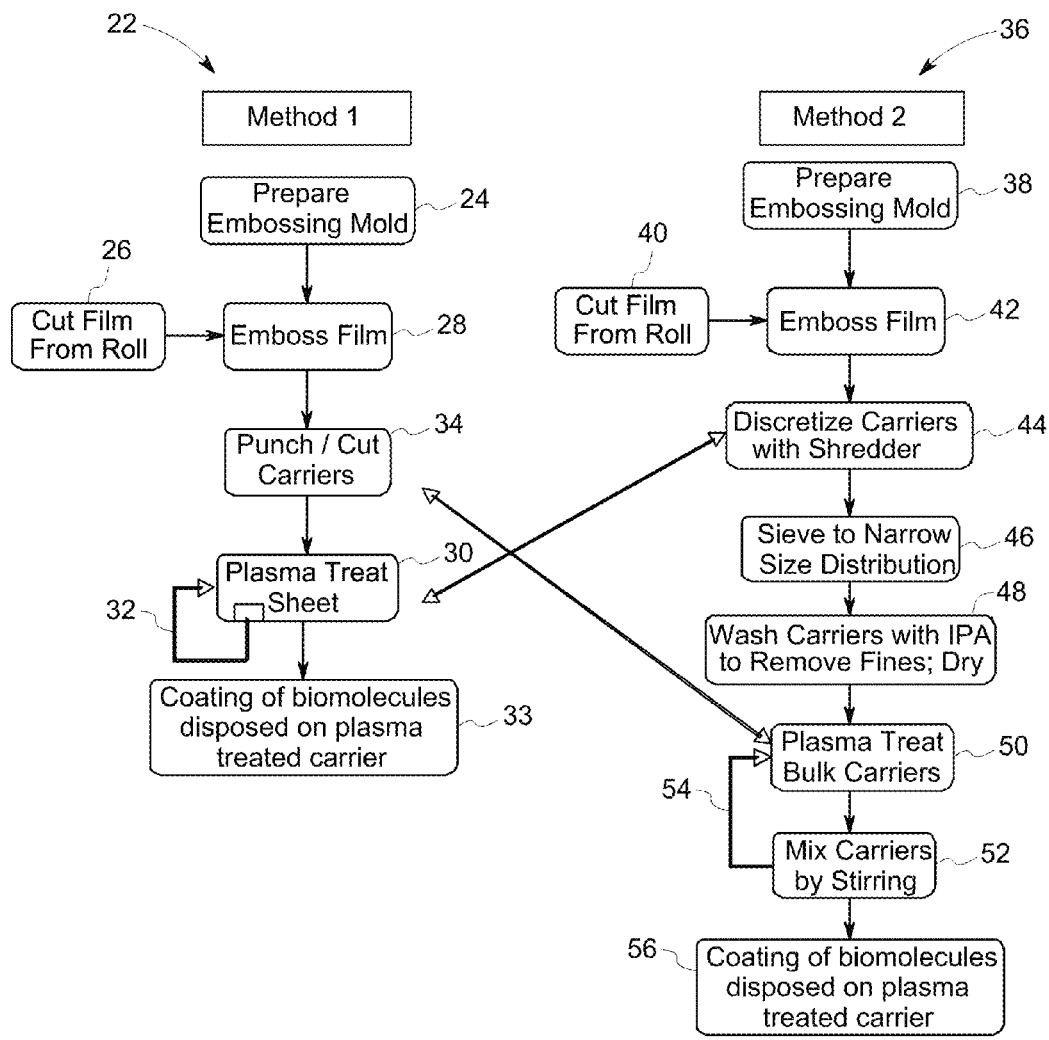
FIG. 4 is another embodiment of a process flow diagram of an example of methods of making carriers of the invention on a small scale in batch mode.

In one example, a process for making a carrier for growing cells is generally illustrated in FIG. 4. The process comprises two alternate methods, method (1) and method (2). The method (1) 22 comprises the steps of preparing embossing mold 24, and cutting a film from a roll 26, followed by embossing the film 28. In some embodiments, the embossed film is obtained from a source and then the film is processed to cut the film into small pieces. In some embodiments, the embossed solid support or film cut 34 into plurality of portions or pieces to form a plurality of embossed carriers. The plurality of embossed carriers further treated with plasma 30 to form plasma treated embossed solid support. In some embodiments, the embossed carriers are optionally plasma treated on the other side of the carriers for better uniformity of treatment 32. In some embodiments, a biomolecular coating is disposed 33 on the plasma treated carriers.

The method (2) also may comprise a method 36 comprising the steps of preparing embossed mold 38, and cutting a film from a roll 40, followed by embossing the film 42. In some embodiments, the embossed film is obtained from a source and then the film is processed to cut the films into small pieces. The embossed film is cut or diced or otherwise discretized to generate embossed pieces 44, which can then be sieved to a narrow size distribution 46. In some embodiments, the carriers are then washed with a wash fluid such as water or a mixture of water and isopropyl alcohol to remove fine particles, followed by drying 48. The carriers are then subjected to a plasma treatment 50 in bulk accompanied by mixing to ensure uniformity of surface treatment 52 to form plasma treated embossed carriers. In some other embodiments, carriers are subjected to a plasma treatment 50 in bulk accompanied by mixing to ensure uniformity of surface treatment 52 to form plasma treated embossed carriers. The plasma treated carriers are then washed with a wash fluid such as water or a mixture of water and isopropyl alcohol to remove fine particles. In some embodiments, a biomolecular coating is disposed 56 on the plasma treated carriers. In some other embodiments, the biomolecular coating directly disposed on the non-plasma treated carriers. The methods (1) and (2) (as described above 22 and 36) can be modified to produce carriers on large scale using roll-to-roll operations for some or all of the steps of manufacturing. For example, the embossing or structure generation step can be scaled-up into a roll-to-roll operation, and the plasma treatment operation can be done in bulk in drum-style plasma reactors treaters, and the discretization can be done via roll-to-roll or sheet-fed cutting operations.

Another example of a method for making the carriers comprises initially providing two flat polymer films. The method further comprises forming one or more structured indentations on the two flat polymer films individually on at least one surface of each of the two films, such as by embossing to make two embossed polymer films (embossed on one side each), and laminating the two embossed polymer films together, back to back, to form a composite laminated embossed polymer film, so that the outwardly facing surfaces comprise one or more of the structured indentations. The laminated embossed polymer film may then be diced to form a plurality of untreated carriers. The untreated carriers are then treated with a plasma treatment to form a plurality of plasma treated carriers. To create structured indentations, the flat polymer films may be alternatively be subjected to casting thermoforming, or injection molding, or a bulk polymer may be made into a solution and cast on a mold to form a film with the structured indentations. In another embodiment, a method comprises initially providing two polymer films with embossed structure on one side (surface) of the film. These two films are provided, laminating the two embossed polymer films together, back to back, to form a composite laminated embossed polymer film, so that the outwardly facing surfaces comprise one or more of the structured indentations.

The structured indentations may be formed in the carrier by one or more of the following methods. In one example, a textured roll is used to make the structured indentations on a heated polymer film in a roll-to-roll process. In another example, a flat mold is prepared by cutting or machining the negative of the desired indentations into a metal block. The metal block then may be used as-is or replicated first as a positive and then as a negative, using, for example, a polymer casting process. The negative mold can then be used in a batch-stamping or hot embossing process to emboss the pattern into a polymer film. In another example, a mold thus formed can be used in a solvent-casting process to make the polymer film with the structured indentations. A polymer solution can be coated on to the mold or textured roll, and dried and/or cured. The dried/cured film then peeled off to yield a film with the desired structured indentations. Alternate methods such as thermoforming or injection molding may also be used.

A cell culture system of the invention uses one or more of the carriers for growing cells. In one embodiment, the cell culture system is a bioreactor, more specifically, an agitated bioreactor. As mentioned herein, a bioreactor may refer to any device or system that supports cell growth. In one aspect, a bioreactor may refer to a device or a system for growing cells or tissues in the context of cell culture or tissue engineering. The bioreactor may employ agitation, generated by an internal impeller or paddle, or via externally rocking, rolling or shaking the culture vessel, or via bellows-induced motion of fluid. The bioreactor may, for example, be a reactor with rocking or rolling motion, such as Wave Bioreactor™, a stirred tank bioreactor, a fluidized bed bioreactor, fixed bed bioreactor, a roller bottle or airlift bioreactor.

The Wave Bioreactor™ comprises a rocking platform supporting a vessel containing a culture fluid, wherein the culture fluid comprises cells in a culture media. The rocking motion of the platform induces mixing and mass transport in the culture fluid. A stirred tank bioreactor generally comprises an impeller system and optionally a sparging system to mix and aerate the culture. An airlift reactor relies on rising gas bubbles to mix and aerate the culture medium. Hydrodynamic factors such as mass transfer, mixing efficiency, and shear stress experienced by cells can be different in the different types of bioreactors. In addition, the cell growth rate and quality of cells may be influenced by operational differences between reactor types.

In another embodiment, the bioreactor may be a stirred tank bioreactor which, under operational condition, comprises a vessel containing the cell growth medium, cells, and carriers. The carriers are agitated through the use of a mechanically or magnetically actuated paddle, screw, impeller or other rotational device (or devices) for mixing the contents of the reactor. Specifically, it is beneficial to ensure that the impeller is raised to a sufficient height above the bottom of the reactor that it does not directly impinge on the bed of carriers. The arrangement of impellers which are raised to a sufficient height above the bottom of the reactor provides two benefits, first, it prevents cells on the carriers from interacting directly with the impeller and generating high local shear and second, it prevents the carriers from becoming bound between the impeller and the vessel walls which may cause high local shear, carrier breakage and hindered proper mixing of the media. Finally, as opposed to traditional bioreactor growth, where shear is not as great of an issue, intermittent, low rate stirring is beneficial in these embodiments as it limits the total amount of potential shear stress of the cells.

The Corning disposable spinner flask is a stirred tank reactor that consists of a 125 mL or 500 mL reservoir, an impeller (paddle) and integrated magnet. The unit comes presterilized, eliminating the need for time-consuming assembly or cleaning and reassembly. The paddle size and height is optimized for different vessel size or volume. The spinner flasks sit on a magnetic induction stirrer that controls the stir rate and provides smooth and even rotation of the impeller. Thus, the hydrodynamic factors including fluidization of the carriers and shear stress can be controlled.

An example of a method of culturing adherent cells comprises providing one or more carriers for growing cells in a bioreactor, adding culture medium, adding an inoculum of cells to the carriers, allowing attachment of cells to the carriers, suspending the carriers in the medium continuously or intermittently, and allowing the cells to grow on the carriers. Cells may be grown in a culture flask or plate prior to addition to the carriers. Cells may also be grown on the carriers directly after extraction and isolation, for example, from blood, bone marrow or tissue section. In some other embodiments, the carriers may be introduced into a spinner flask, a stacked culture flask, a stirred tank reactor, a Wave Bioreactor™ or any other in-vitro cell culture system.

Cultured cells may be detached or released from the carriers by a variety of methods. The cells may be released, for example, by using a mechanical method, an enzyme, a thermoresponsive polymer, a pH responsive polymer or a combination thereof. The cell release by mechanical method includes cell scraping. The cells may also be released by treating with proteolytic enzymes, such as trypsin. One non-enzymatic method uses calcium chelators, such as EDTA. Other non-enzymatic methods include, but are not limited to, physical methods that use ultrasound, which generates bubbles that facilitate cell detachment. Cultured cells from carriers comprising thermoresponsive polymers, such as poly-N-isopropylacrylamide (PNIPAAm) may be released by cooling the carrier to a temperature below LCST.

The carriers can be used in combination with a bioreactor or culture vessel, to provide or enhance surface area for the attachment and growth of anchorage-dependent cells. Some embodiments of the kit of the invention for culturing cells comprise a disposable housing or vessel pre-loaded with one or more carriers. In one embodiment, the carriers and the disposable housing or vessel may be provided separately. In one embodiment, the housing may be reusable. The housing may be, for example, a bag, a flask, a tank, a tube, a petridish or a bottle. The kit may further comprise culture media suitable for cell growth. The kit may comprise cells in a frozen condition and may further comprise a protocol for using the carriers.

The present embodiments provide culture and release of multipotent and pluripotent cells with high purity, high efficiency and high yield. The plasma coated engineered surface, such as embossed surface that may protect the adherent, shear-sensitive cells, such as human pluripotent stem cells (hPSCs) which include human embryonic stem cells (hESC) or human induced pluripotent stem cells (hiPSC). In one or more embodiments, human pluripotent stem cells (e.g. embryonic stem cells) are seeded onto the polystyrene carriers, which protect the cells from fluid induced shear that may result in cell death and differentiation, specifically when the cells are cultured in a bioreactor. In the absence of shear forces, the hESCs may be able to grow and expand maintaining the pluripotency. In one or more embodiments, the carriers are easily separable from the cultured hESCs. The density of the carriers may be slightly higher than the density of the growth medium.

The cell culture carrier of the present invention may greatly extend the proliferative capacity of different primary cells isolated from tissues and various stem cells from bone marrow, cord blood, adult blood, or adipose tissue. The expansion of such cells greatly facilitates various applications, such as, transplantation, tissue engineering, etc. using autologous or allogenic cell sources. Sufficient expansion and recovery of adult stem cells may overcome the limitations of using adult stem cells for various applications. The sufficient expansion and subsequent differentiation of adult derived pluripotent stem cells such as induced pluripotent stem cells or trans-differentiated cells can replace the embryonic stem cells which may address the ethical issue for using the embryonic stem cells for various applications. Different methods for derivation of human embryonic stem cell lines without destruction of embryos are reported. The methods may include a single blastomere biopsy method for isolating hES cells from single blastomere without destroying the embryo, or a technique similar to pre-implantation genetic diagnosis adapted for removing blastomeres, wherein the procedure did not appear to interfere with subsequent blastocyst development of the parent embryo.

Example 1

Fabrication of Carrier for Growing Cells

Method of Making a Pattern Master—

A pattern-master was prepared by cutting grooves in a flat aluminum block using a dicing saw, which is outfitted with a resin-bonded diamond blade. A set of parallel grooves (the term being interchangeably used with 'indentations') was first cut in one direction, then a second set of parallel grooves was cut perpendicular to the first set of grooves. Finally, an effort was made to remove burrs that had formed in the first set of grooves during the cutting process. After the grooves were completed, the aluminum block was cleaned to remove any burrs on its surface. The pattern master determined the pattern geometry of the embossed carriers.

Formation of First Generation Mold from the Pattern Master—

A first-generation mold was then made from the pattern-master using a fluorosilicone rubber, FSL 7661 (purchased from Momentive Performance Materials, Waterford, N.Y.). To produce the first-generation mold, the two part fluorosilicone compound was mixed at a 1:1 ratio according to directions from the manufacturer, using a Hauschild Speed-Mixer. The pattern-master was placed in a hollowed-out Teflon block and uncured fluorosilicone was applied, in excess, on the surface of the pattern master. A chrome-plated steel plate was placed on top of the fluorosilicone, and the fluorosilicone was cured in a heated hydraulic press at 4000 lb force and 170° C. for 30 minutes. After cooling to room temperature, the cured fluorosilicone rubber-based first-generation mold was removed from the pattern-master and cured overnight at 200° C. in air.

Formation of Second Generation Mold from the Pattern Master—

Two second-generation molds were then prepared using a silicone rubber-molding compound, RTV 664 (purchased from Momentive Performance Materials, Waterford, N.Y.) from the first-generation mold as mentioned above. The silicone compound was mixed at a 10:1 ratio according to directions from the manufacturer, using a Hauschild Speed-Mixer. The first-generation mold was placed inside a steel frame with the patterned surface up and the silicone compound was dispensed, in excess, on the first-generation mold. A flat stainless steel plate was placed on top of the silicone and the silicone was cured in a heated hydraulic press at 1000 lb force and 120° C. for 30 minutes. After cooling to room temperature, the cured silicone rubber second-generation mold was removed from the fluorosilicone first-generation mold.

Method of Making Embossed Polystyrene Sheets—

Multiple sheets of biaxially oriented polystyrene film (Trycite 1003U, Dow Chemical Company) were placed in between two second-generation molds with patterns facing in. The number of sheets of film was chosen so that the volume of polystyrene was sufficient to fill the pattern in the second-generation molds and still leave a small amount of polystyrene separating the molds. The films were then embossed (28, FIG. 3) in a heated hydraulic press with 1000 lb force and a temperature cycle that ramped up to 150° C. for 5 minutes and then cooled to below 60° C. The embossing process fused the multiple sheets of film into a single monolithic structure that replicated the texture of the molds and pattern-master on both sides. The embossed polystyrene film was removed from the molds after cooling to room temperature.

Chemical Treatment of the Embossed Film Surface—

To make the embossed polystyrene film compatible with cell growth, the film was $O_2$ plasma treated (30, FIG. 3) using a Plasma Therm SLR vacuum plasma reactor as mentioned in FIG. 3. Plasma treatment was performed on each side of the embossed film for 1 minute at 100 mtorr pressure using 100 sccm (Standard Cubic Centimeters per Minute) $O_2$ flow and 100 W forward radio frequency (RF) power in reactive ion etching (RIE) mode.

Dicing of the Film to Generate Carrier—

Carriers for cell culture were prepared from the plasma-treated embossed sheets either by manually cutting the film into 6.5 mm×6.5 mm pieces or 2 mm×2 mm pieces, or by discretizing (44) and then sieving (46) to select a particular size range, or by punching circular discs of the desired size.

Variants of the Carrier Fabrication Process—

In some instances, a ceramic block was used in place of the aluminum block to make the pattern-master. A pattern-master was prepared by cutting grooves in a flat alumina block (99.6% alumina, fired, 20-25 μm polish from Acumet) using a dicing saw outfitted with a resin-bonded diamond blade. A set of parallel grooves was first cut in one direction, and then a second set of parallel grooves was cut perpendicular to the first set of grooves. The geometry of the pattern master determined the pattern geometry of the eventual embossed carriers. When the ceramic block was used, the first-generation mold was prepared slightly differently. Instead of the Teflon block, a steel frame was used to hold the ceramic pattern-master. The curing was performed at a higher temperature, 170° C. for 15 minutes and then 200° C. for 15 minutes. The rest of the procedure remained the same as described above.

In some examples, the fluorosilicone first-generation molds were replaced with RTV silicone first-generation molds. The procedure was modified as described below. A first-generation mold was then made from the pattern-master using a silicone rubber-molding compound, RTV 664 from Momentive Performance Materials. To produce the first-generation mold, the silicone compound was mixed at a 10:1 ratio according to directions from the manufacturer, using a Hauschild SpeedMixer. The pattern-master was placed in a hollowed-out Teflon block and uncured silicone compound was applied, in excess, across the surface of the pattern master. A chrome-plated steel plate was placed on top of the silicone, and the silicone was cured in a heated hydraulic press at 1000 lb force and 120° C. for 30 minutes. After cooling to room temperature, the cured silicone rubber first-generation mold was removed from the pattern-master. The first generation mold was coated with (tridecafluoro-1,1,2,2-tetrahydrooctyl) trichlorosilane by vacuum deposition at 750 mtorr for 45 minutes prior to making any second-generation molds. Cell carriers of different designs were made using the above fabrication procedures. The embossed cell carriers of the invention may include carriers with alternate wall shape. For example, carriers with rectangular shaped walls were made, and carrier with triangular shaped wall in cross-section were made.

Example 2

Qualitative and Quantitative Estimation of Cell Growth

Materials: The materials used for the subsequent examples include centrifuge tubes, disposable spinner flasks and Synthemax® II substrates purchased from Corning® (MA, USA). Matrigel™ matrix was purchased from BD Biosciences. Laminin 521 was purchased from BioLamina (Stockholm, Sweden). Accutase™ was purchased from MP Biomedical (CA, USA) and Invitrogen™ (NY, USA); TrypLE was purchased from Invitrogen (NY, USA). mTeSR™-1 medium was purchased from STEMCELL™ Technology Inc. (Vancouver, BC, Canada). Y-27632 (ROCK Inhibitor) was purchased from Sigma Aldrich (St. Louis, Mo.) and Millipore®.

Cell Carriers—

The carriers used for the following examples had a length and width of 6.5 mm, and a height of about 0.5 mm. The carriers comprised a plurality of structured indentations on each of the two outer surfaces. Each of the structured indentations had a major axis and minor axis of 0.45 mm each and a depth of 0.2 mm. The carriers used for the majority of experiments using hESC were 6.5 mm hexagonal carrier with height of 50 micron.

Cells:

CT-2 cell line (human embryonic stem cells) was obtained from University of Connecticut, USA; CHB-10 cell line was obtained from George Daley, Children's Hospital Boston, USA; the H1 and H7 cell lines were obtained from Geron Corporation.

Cell Staining and Imaging—

Samples for imaging were fixed at room temperature in 4% paraformaldehyde (PFA), which is freshly diluted in PBS from a 16% stock, stored in presence of argon in an amber glass vial. Once fixed, samples were stored at 4° C. until they were stained and imaged. Fixed cells were stained with Hoechst 33342 dye (from Invitrogen) or 4',6-diamidino-2-phenylindole (DAPI) to highlight the nuclei and with phalloidin-Alexa-568 (from Invitrogen) to visualize the cytoskeleton (actin) after permeabilization with 0.1% Triton X-100 detergent (Sigma). The stained cells were imaged with an Nikon Eclipse TE2000-U inverted fluorescence microscope, wherein the microscope was fitted with appropriate filter cubes and light source for the fluorophores being used.

Cell Viability Measurement by CellTiter-Glo®—

Cell growth and morphology was assessed at intervals by taking samples of carriers and either measuring total ATP content or fixing and staining for fluorescence microscopy. Cell growth was assayed by CellTiter-Glo® luminescent cell viability assay reagent from Promega, which determines the number of viable cells in culture based on quantitation of the ATP present, which signals the presence of metabolically active cells. The process involves adding a single reagent (CellTiter-Glo®) directly to cells cultured in serum-supplemented medium. The homogeneous reagent results in cell lysis and generation of luminescent signal proportional to the amount of ATP present. The amount of ATP is directly proportional to the number of cells present in the culture. The assay relies on thermostable luciferase, which generates a stable 'glow type' luminescent signal resulting from oxyluciferin catalysed by luciferase in presence of $Mg^{+2}$, ATP, and molecular oxygen. After 10 minutes of the cell lysis, 200 μL aliquots of cell lysate were transferred to an opaque 96-well plate, mixed gently and read in a SpectraMax® luminescence microplate reader from Molecular devices to generate readings for cell viability. Luminescence readings from this assay are proportional to the number of viable cells present in the sample and so can be used to monitor the progress of cell growth.

Example 3

Preparation of Plasma Treated Carriers

Carriers were embossed on both sides with 650 nm pitch waffle pattern (450 nm square well size with a depth of 200 μm) and cut into hexagonal pieces (0.25" edge-to-edge width). Carriers were plasma treated as a 1135 g batch the embossed carriers were plasma treated in a custom-made rotating drum plasma system with a central rod anode, at 25° C. The plasma was generated at 500 W with a 1000 sccm flow of $O_2$ for 18 minutes with a rotation rate of about 5 rpm. The plasma treated carriers were stored at room temperature and ambient humidity for approximately one month before aliquots were prepared (1.17 g/batch) in polypropylene 50 mL centrifuge tubes. Each aliquot was washed thrice with isopropanol, four times with 18.2 MΩ deionized water and thrice with 70% Ethanol/$H_2O$ (vol./vol.).

Example 4

Preparation of Matrigel™ Coated Carriers

The plasma treated carriers (from Example 13) were transferred under sterile conditions to a Corning 125 mL disposable spinner flask (#3152). The Ethanol/Water sterilization solution was pipetted off and the carriers were washed twice with PBS. The carriers were then coated with 7 mL of BD Matrigel™ diluted 1:20 in DMEM/F12 for 60 minutes with mixing every 20 minutes, followed by 0 or 1 wash with PBS.

Example 5

Cell Culture on the Coated Carriers

The coated carriers were used for cell culture applications. Human embryonic stem cells (CT2 cell line, University of Connecticut) were grown on a Matrigel™ coated 6-well tissue culture polystyrene plate for one passage prior to this experiment. Cells were washed once with phosphate buffered saline (PBS) and treated with Accutase™ for three minutes at 37° C. Cells were centrifuged at 200 G for 5 minutes and re-suspended in mTeSR-1 medium. Cells were counted on a NucleoCounter NC-100 (Chemometec, Denmark).

The cells were seeded onto the Matrigel™-coated carriers in the spinner flask at a concentration of $4 \times 10^6$ cells/100 $cm^2$ projected surface area (1.17 g aliquot) in 50 ml mTeSR™-1 with 10 μM Y-27632 (ROCK® Inhibitor). The cells were cultured with 1 minute of stirring at 60 rpm followed by 45 minutes static over the course of three days after seeding. Each day, half of the media was removed and replaced with fresh mTeSR™-1. On the final day, the cells were harvested from the spinner flasks. First, the media was removed, followed by a PBS wash, followed by the addition of 7 mL of Accutase™ which was gently stirred and returned to the incubator for six minutes. The suspended cells were removed and the carriers were washed with PBS to remove the remaining cells. The cells were then centrifuged at 200 G for 5 minutes and re-suspended in mTeSR™-1 for counting via Nucleocounter. $23.4 \times 10^6$ live cells were recovered, for a fold expansion of 5.85 with a viability of 89.3%.

Example 6

Effect of Contact Angle on Cell Culture

The carriers were plasma treated in two different batches under two different conditions. The carriers, plasma treated under two different conditions, resulted in different contact angles. One batch (batch A) of the embossed carriers was plasma treated 24 hours prior to use at 25° C. as a 15 g batch (batch A) using a parallel plate radio frequency plasma treatment system (PlasmaTherm SLR 740) at 100 W, 100 sccm $O_2$ gas, 100 mTorr Pressure for one minute. The plasma treatment procedure was repeated five times with the carriers removed and shaken to rearrange the carriers between each run. Within 24 hours, the plasma treated samples were massed into aliquots (1.17 g/batch) in polypropylene 50 mL centrifuge tubes (Corning), and washed thrice with isopropanol, four times with 18.2 MΩ deionized water and thrice with 70% Ethanol/$H_2O$ (vol/vol). The final wash solution was left in place and the plasma treated carriers were transferred to other container. Another batch (batch B) was prepared as a 1135 g plasma treatment run in a custom-made rotating drum plasma system with a central rod anode, at 25° C. The plasma was generated at 500 W with a 1000 sccm flow of $O_2$ for 18 minutes with a rotation rate of about 5 rpm. The plasma treated carriers were stored at room temperature and ambient humidity for approximately one month before aliquots were prepared (1.17 g/batch) in polypropylene 50 mL centrifuge tubes. Each aliquot was washed thrice with isopropanol, four times with 18.2 MΩ deionized water and thrice with 70% Ethanol/$H_2O$ (vol./vol.). The carriers of batch A which were plasma treated 24 hours before use, generated a lower contact angle of about 20° on disposition of a 1 μL droplet of water on a flat polystyrene piece treated alongside the carriers than the carriers from batch B, which generated a higher contact angle of about 72° which were allowed to age for a month before use The carriers from both of the batches A and B, were then coated with Matrigel™ as mentioned in Example 14. hESCs (CT-2 cell line) were grown on Matrigel™-coated carriers generated from both the batches as described in Example 15. The cells were then centrifuged at 200 G for 5 minutes and re-suspended in mTeSR-1 for counting via NucleoCounter NC-100. The cells were grown on the carriers from batch A and were recovered $23.4 \times 10^6$ live cells, a 5.85 fold expansion, and with a viability of 89.3%. The cells were grown on the carriers from batch B and were recovered an average of 33 (±3)$\times 10^6$ live cells, a fold expansion of 8.3 (±0.8) with a viability of 90% (n=3). The effect of contact angle on cell expansion is represented in Table 1.

TABLE 1

Effect of contact angle on cell growth

| Sample | Contact angle | Recovered live cells | Fold expansion | Viability |
|---|---|---|---|---|
| Batch B | High (72°) | 33 (±3) × $10^6$ | 8.3 (±0.8) | 90% |
| Batch A | Low (20°) | 23.4 × $10^6$ | 5.85 | 89.3% |

Example 7

Small Molecule Peptide Coating (Corning Synthemax® II)

Carriers were embossed on both sides with 650 nm pitch waffle pattern (450 nm square well size with a depth of 200 nm) and cut into hexagonal pieces (0.25" edge-to-edge width). Carriers were plasma treated as a 1135 g batch in a custom-made rotating drum plasma system with a central rod anode. The plasma was generated at 500 W with a 1000 sccm flow of $O_2$ for 18 minutes with a rotation rate of about 5 rpm. Carriers were stored at room temperature and ambient humidity for approximately one month before aliquots were prepared (1.17 g/batch) in polypropylene 50 mL centrifuge tubes (Corning). Each aliquot was washed thrice with isopropanol, four times with 18.2MΩ deionized water and thrice with 70% Ethanol/$H_2O$ (vol/vol). The final wash solution was left in place and the samples were used for cell growth.

The carriers were transferred under sterile conditions to a Corning 125 mL disposable spinner flask (#3152). The Ethanol/Water sterilization solution was pipetted off and the carriers were washed twice with PBS. Synthemax® II-SC powder was reconstituted with 10 ml sterile water to generate a stock of 1 mg/ml. A dilution of 1:40 in sterile water was used to create the working solution. 20 ml of the Synthemax®II-SC working solution was used to coat 100 $cm^2$ carriers at 37° C. for 2 h.

Human embryonic stem cells (CHB-10 cell line, received from George Daley, Children's Hospital Boston) were grown on a Matrigel™ coated 6-well tissue culture polystyrene plate for six passages and on Synthemax® II for an additional passage prior to this experiment. Cells were washed once with PBS and treated with Accutase™ for three minutes at 37° C. Cells were centrifuged at 200 G for 5 minutes and re-suspended in mTeSR-1 medium. The cells were counted on a NucleoCounter NC-100 (Chemometec, Denmark). Then the cells were seeded onto the Synthemax® II coated carriers in the spinner flask at a concentration of $3 \times 10^6$ cells/100 $cm^2$ projected surface area (1.17 g aliquot) in 50 mL mTeSR™-1 with 10 μM Y-27632 (ROCK Inhibitor). The cells were seeded with intermittent stirring at 40 rpm with a 1 minute on/10 minute off cycle for one hour, followed by 1 minute on/45 minutes off at 25 rpm over the course of four days after seeding. On the second day after seeding, half of the media was removed and replaced with fresh mTeSR™-1. On the final day, the spinner flasks were harvested. First, the media was removed, followed by a PBS wash, followed by the addition of 7 mL of Accutase™ which was gently stirred and returned to the incubator for six minutes. The suspended cells were removed and the carriers were washed with PBS to remove the remaining cells. The cells were then centrifuged at 200 G for 5 minutes and re-suspended in mTeSR™-1 for counting via Nucleocounter. $5.39 \times 10^6$ live cells were recovered, for a fold expansion of 1.8 with a viability of 84.2%.

Example 8

Recombinant Protein Coating (Laminin 521)

Carriers were embossed on both sides with 650 nm pitch waffle pattern (450 nm square well size with a depth of 200 μm) and cut into hexagonal pieces (0.25" edge-to-edge width). Carriers were plasma treated as a 1135 g batch in a custom-made rotating drum plasma system with a central rod anode. The plasma was generated at 500 W with a 1000 sccm flow of 02 for 18 minutes with a rotation rate of ~5 rpm. Carriers were stored at room temperature and ambient humidity for approximately one month before aliquots were prepared (1.17 g/batch) in polypropylene 50 mL centrifuge tubes (Corning). Each aliquot was washed thrice with isopropanol, thrice with 18.2MΩ deionized water and thrice with 70% Ethanol/$H_2O$ (vol/vol). The final wash solution was left in place and the samples transferred to the biology lab for cell growth.

The carriers were transferred under sterile conditions to a Corning 125 mL disposable spinner flask (#3152). The Ethanol/Water sterilization solution was pipetted off and the carriers were washed twice with PBS. Laminin 521 (LM 521) was diluted with pre-warmed 1×PBS to a final concentration of 20 ug/ml to form a laminin 521 coating solution. 7 mL of Laminin 521 coating solution was used to coat 100 cm² carriers for 2 h at 37° C. After the coating, LM521 was slowly removed and the carriers were washed with warm PBS. The LM521 solution was collected in a sterile tube and reused for up to two additional coatings without loss of biological activity.

Human embryonic stem cells (CHB-10 cell line) were grown on a Matrigel™ coated 6-well tissue culture polystyrene plate for seven passages prior to this experiment. Cells were washed once with phosphate buffered saline (PBS) and treated with Accutase™ for three minutes at 37° C. Cells were centrifuged at 200 G for 5 minutes and re-suspended in mTeSR-1 medium. Cells were counted on a NucleoCounter NC-100 (Chemometec, Denmark). The cells were seeded onto the Laminin 521 coated carriers in the spinner flask at a concentration of $3 \times 10^6$ cells/100 cm² projected surface area (1.17 g aliquot) in 50 ml mTeSR-1. Of note, Y-27632 (ROCK Inhibitor) was not added to the medium. The cells were seeded with intermittent stirring at 40 rpm with a 1 minute on/10 minute off cycle for one hour, followed by 1 minute on/45 minutes off at 25 rpm over the course of four days after seeding. On the second day after seeding, half of the media was removed and replaced with fresh mTeSR-1. On the final day, the cells were harvested from the spinner flasks. First, the media was removed, followed by a PBS wash, followed by the addition of 7 mL of Accutase™ which was gently stirred and returned to the incubator for six minutes. The suspended cells were removed and the carriers were washed with PBS to remove the remaining cells. The cells were then centrifuged at 200 g for 5 minutes and re-suspended in mTeSR™-1 for counting via Nucleocounter. $7.02 \times 10^6$ live cells were recovered, for a fold expansion of 2.34 with a viability of 85.5%.

Example 9

Seeding and Expansion of Human Pluripotent Stem Cells from Different Sources

Human embryonic stem cells (CHB10, CT2, H1 and H7) were released from a substrate (e.g., plate, flask, dish, carrier) using enzymatic or non-enzymatic methods. The released cells existed as single cells and/or clusters of cells. Cells in suspension were added to a vessel (e.g., bioreactor, flask, roller bottle, bottle, tube) mixed with carriers for seeding the cells onto the carriers. The vessel can be mixed or kept static during the seeding step. Cells seed onto both the upper and lower side of the embossed carriers, and mixing encourages uniform cell distribution onto both sides of the carrier. For example, cells released using Accutase™ or TrypLE (Invitrogen™) and re-suspended in mTesR™-1 were mixed with Matrigel™ coated carriers in a Corning disposable spinner flask with 10 μM Y-27632 (ROCK Inhibitor). The cells and carriers were then stirred continuously at 25-60 rpm for 15 minutes to 2 hours, or stirred intermittently (1 minute at 25-60 rpm with 5 to 45 minute static) for 1 to 3 hours. Following the seeding protocol, cells were expanded for up to 6 days before harvest, using intermittent stirring conditions (e.g. 1 minute of stirring at 25 to 60 rpm and 10 to 45 minute rest periods without stirring). The cell culture medium was exchanged every 1 or 2 days, in which 50% to 100% of the medium was exchanged with fresh medium without Y27632 ROCK Inhibitor. Typical colony growth on the carriers of the invention in spinner flasks as shown in FIGS. 5 A and 5 B. FIGS. 5 A and 5 B are optical microscopy images (40× magnification) demonstrating seeding and expansion of CT2 cells grown on the carriers of the invention in spinner flasks after 4 hours of seeding and after 3 days of seeding respectively. Colonies were stained with phalloidin and DAPI to enhance visualization.

In one example, $3 \times 10^6$ CHB10 (Children's Hospital Boston) cells were mixed with 100 cm² Matrigel™ coated carriers in a Corning 125 mL disposable spinner flask (#3152). The contents were then stirred at 60 rpm for 15 minutes, then stirred intermittently (1 minute stirred at 25 rpm, 45 minute static) for 4 days, resulting in 6.8-fold expansion of viable cells.

In another example, $4 \times 10^6$ CT2 cells were mixed with 100 cm² Matrigel™ coated carriers in a Corning 125 mL disposable spinner flask (#3152). The contents were then stirred at 60 rpm for 15 minutes, then stirred intermittently (1 minute stirred at 25 rpm, 45 minute static) for 3 days, resulting in 4.0-fold expansion of viable cells.

In another example, $1.1 \times 10^6$ CT2 cells were mixed with 100 cm² Matrigel™ coated carriers in a Corning 125 mL disposable spinner flask (#3152). The contents were then stirred intermittently (1 minute at 40 rpm, 10 minute static) for 1 hour, then stirred intermittently (1 minute stirred at 25 rpm, 45 minute static) for 5 days, resulting in 18.8-fold expansion of viable cells.

In another example, $6.8 \times 10^6$ H1 cells were mixed with 225 cm² Matrigel™ coated carriers in a Corning 125 mL disposable spinner flask (#3152). The contents were then stirred intermittently (1 minute at 40 rpm, 10 minute static) for 1 hour, then stirred intermittently (1 minute stirred at 25 rpm, 45 minute static) for 4 days, resulting in 3.0-fold expansion of viable cells.

In another example, $10 \times 10^6$ CT2 (University of Connecticut) cells were mixed with 400 cm² Matrigel™ coated carriers in a Corning 125 mL disposable spinner flask (#3152). The contents were then stirred intermittently (1 minute at 40 rpm, 5 minute static) for 1 hour, then stirred intermittently (1 minute stirred at 25 rpm, 45 minute static) for 4 days, resulting in 4.8-fold expansion of viable cells.

In another example, $15 \times 10^6$ CT2 cells (University of Connecticut) were mixed with 500 cm² Matrigel™ coated carriers in a Corning 500 mL disposable spinner flask (#3153). The contents were then stirred intermittently (1 minute at 40 rpm, 10 minute static) for 1 hour, then stirred intermittently (1 minute stirred at 25 rpm, 45 minute static) for 4 days, resulting in 6.6-fold expansion of viable cells. The fold expansion of different cell types is presented in Table 2.

TABLE 2

Fold expansion of different pluripotent stem cell lines

| Cell line | No. of cells seeded | Culture time | Carrier size (cm²) | Fold expansion |
|---|---|---|---|---|
| CHB10 | $3 \times 10^6$ | 4 days | 100 | 6.8 |
| CT2 | $4 \times 10^6$ | 3 days | 100 | 4.0 |
| CT2 | $1.1 \times 10^6$ | 5 days | 100 | 18.8 |
| H1 | $6.8 \times 10^6$ | 4 days | 225 | 3.0 |
| CT2 | $10 \times 10^6$ | 4 days | 400 | 4.8 |
| CT2 | $15 \times 10^6$ | 4 days | 500 | 6.6 |

Example 10

Human Pluripotent Stem Cell Expansion on Carriers

Cells cultured on carriers in stirred tank reactors were maintained for up to 6 days before harvest, using intermittent stirring conditions (e.g. 1 minute of stirring at 25 to 60 rpm and 10 to 45 minute rest periods without stirring). The cell culture medium was exchanged every 1 or 2 days, in which 50% to 100% of the medium was exchanged with fresh medium, and cells were harvested 3 to 6 days after seeding. In one example, 50% of the medium was exchanged on days 2 and 3 of culture, and cells were harvested on day 4. Cells expand as monolayers on the carriers with minimal to no three-dimensional growth. Upon reaching confluency, the cells continue to grow and colonies begin to form three-dimensional clusters, reducing cell viability and reducing seeding efficiency in the next passage.

FIGS. 6 A to 6 D show fold-expansion and cell viability for H1, H7, CT2 and CHB10 human embryonic stem cells serially passaged on carriers in Corning disposable spinner flasks. FIGS. 6 A to 6 D are a series of graphs representing expansion and viability of human pluripotent stem cells grown on the carriers in spinner flasks during continuous serial passage. Cells were enzymatically recovered from the carriers, counted, then reseeded onto new carriers for ten or more passages, demonstrating reproducible expansion rates and maintenance of viability during serial passages. FIGS. 6 A, 6 B, 6 C and 6 D represent the growth of CHB10, CT2, H1 and H7 cells respectively on the carriers in spinner flask. The average fold-expansion for H1, H7, CT2 and CHB10 human embryonic stem cells on carriers are presented in Table 3.

TABLE 3

Average fold-expansion of cells maintained in serial passage on carriers of the invention in spinner flasks.

| Cell line | Average 3-day expansion | Average 4-day expansion |
|---|---|---|
| CHB10 | 3-fold expansion | 6.1-fold expansion |
| CT2 | 3.2-fold expansion | 7.9-fold expansion |
| H1 | 2.7-fold expansion | 4.2-fold expansion |
| H7 | 2.1-fold expansion | 3.3-fold expansion |

Example 11

Human Pluripotent Stem Cell Recovery from Carriers

Human embryonic stem cells (CHB10, CT2, H1 and H7) were released from shear protected carriers using enzymes such as Accutase™, TrypLE, Trypsin, Thermolysin, Liberase, and non-enzymatic solutions such as Versene and EDTA. In one example, near complete removal of cells was accomplished using 7 mL of Accutase™ after 6 minute incubation. Cell removal was enhanced by agitating the stirred tank reactor and by pipetting. Typical viabilities of 90% (range 85% to 97%) were obtained when using Accutase™ to recover CHB10, CT2, H1 and H7 human embryonic stem cells from the carriers.

In another example, near complete removal of cells was accomplished using 7 mL of Accutase™ (MP or Invitrogen) diluted 1:5 with PBS after a 6 minute incubation. Cell removal was enhanced by agitating the stirred tank reactor and by pipetting. 92% viability was observed in CT2 human embryonic stem cells from the carriers.

In another example, near complete removal of cells was accomplished using 7 mL of TrypLE™ (Invitrogen™) diluted 1:5 with PBS after a 6 minute incubation. Cell removal was enhanced by agitating the stirred tank reactor and by pipetting. Typical viabilities of 98% (range 97% to 99%) were obtained when using TrypLE™ to recover CHB10 and CT2 human embryonic stem cells from the carriers.

Example 12

Confirmation of Pluripotency after 10 or More Serial Passages of Human Pluripotent Stem Cells Cells were maintained on carriers in stirred tank reactors for 10 or more serial passages, then analyzed for Oct4 and Tra-1-60 expression by flow cytometry, Oct4 and SSEA4 expression by immunocytochemistry, karyotype and for three germ layer differentiation from embryoid bodies. In one example, CHB10 and CT2 cells were serially passaged for 10 or more passages on carriers in stirred tank reactors, then were re-plated onto 6-well, 12-well, 24-well plates, T25 flasks and/or T75 flasks. Cells were fixed in 4% paraformaldehyde and permeabilized in 0.1% Triton X-100, then analyzed by flow cytometry using an Oct4 antibody (BD Pharmingen) conjugated with AlexaFluor 647 and Tra-1-60 antibody (BD Pharmingen) conjugated with R-Phycoerythrin (PE). Results as shown in FIGS. 7 A to 7 E demonstrate maintenance of pluripotency markers after serial passage on the carriers in the spinner flasks. FIGS. 7 A to 7 E show a flow cytometric evaluation of the pluripotency markers Oct4 and Tra-1-60 expression on CT2 cells serially passaged on the carriers of the invention in stirred tank reactors over 2, 10 and 19 passages as shown in FIGS. 7 F, 7 G and 7 H respectively. FIG. 7 A shows the axis for Oct 4 and Tra-1-60, FIG. 7 B shows forward scatter and side scatter properties of the cells, FIG. 7 C is a negative control without staining the cells, FIG. 7 D shows staining with isotype antibodies and FIG. 7 E shows pluripotency marker expression in static culture. The data demonstrates maintenance of pluripotency over 19 passages on the carriers of the invention in spinner flasks.

CT2 and CHB10 cells were fixed in 4% paraformaldehyde and permeabilized in 0.1% Triton X-100, then analyzed using an Oct4 antibody (Cell Signaling) conjugated with AF555 and SSEA4 antibody (Cell Signaling) conjugated with AF647. Results as shown in FIGS. 8 A to 8 F demonstrate maintenance of pluripotency markers after serial passage on the carriers in the spinner flasks. Cells expanded on the carriers in spinner flasks demonstrated normal karyotype. FIGS. 8 A to 8 F represent a series of 100× optical microscopy images of CT2 cells maintained for 10 passages on the carriers in spinner flasks. FIGS. 8 G to 8 I represent a series of 200× optical microscopy images of CHB10 cells maintained for 22 passages on the carriers in spinner flasks. After 10 passages, cells were probed with antibodies against SSEA4 (FIGS. 8 A, 8 D and 8 G), Oct4 (FIGS. 8 B, 8 E and 8 H), and stained with DAPI (FIGS. 8 C, 8 F and 8 I). The colonies strongly expressed the pluripotency markers SSEA4 and Oct4, demonstrating maintenance of pluripotency when expanded on the carriers in the spinner flasks.

Cells were plated to promote differentiation after forming embryoid body aggregates. The differentiated cells were fixed overnight in 10% Formalin, embedded in paraffin, cut into 5-μm serial sections, and immunohistochemistry (IHC) staining was performed using anti-alpha-fetoprotein (endoderm), anti-smooth muscle actin (mesoderm) and anti-tubulin III (ectoderm). Differentiated cells were stained positive for all antibodies, suggesting maintenance of pluripotency during serial passage on the carriers in spinner flasks.

Example 13

Comparison of Embossed Carriers to Flat and Spherical Microcarriers

Human embryonic stem cells grown on commercial microcarriers (Prototype I, Prototype II, and Prototype III) exhibited carrier-to-carrier bridging, resulting in large clusters, three-dimensional colony growth, and reduced cell viability and recovery (FIGS. 9A to 9 D). Rapid separation of cells from the commercial carriers proved challenging due to the small size of the carriers and their slow rate of gravity settling. FIGS. 9 A to 9 D represent a series of 40× optical microscopy images of CT2 cells grown on commercial microcarriers (FIGS. 9 A to 9 C) and the carriers of the invention (FIG. 9 D) in spinner flasks. In detail, FIGS. 9 A, 9 B and 9 C represent significant human pluripotent stem cell bridging across the microcarriers resulted in microcarrier clustering and three dimensional cell growth on the prototype I, prototype II and prototype III respectively. Colonies grown on the carriers of the invention in spinner flasks expand as a monolayer without promoting carrier clustering or three dimensional cell growth, as shown in FIG. 9 D. The embossed carrier design solves many of the challenges that occur when culturing pluripotent cells on traditional microcarriers by providing shear protection, allowing easy separation of the carriers from cells during passaging, and preventing the formation of cell-carrier aggregates as shown in Table 4.

In one example, Prototype I microcarriers were coated with 7 mL of Matrigel™ (BD) diluted 1:20 in DMEM/F12 for 60 minutes with mixing every 20 minutes, followed by 0 or 1 washes with PBS. CT2 cells were seeded onto the Matrigel™-coated carriers in the spinner flask at a concentration of 4×10⁶ cells/100 cm² carriers in 50 ml mTeSR-1. The cells were seeded with continuous stirring at 40 rpm for 15 minutes, followed by a 1 minute on/45 minutes off cycle at 40 rpm over the course of four days after seeding. FIG. 9 A shows CT2 cells grown on commercial microcarrier of prototype I in spinner flask. On the second day after seeding, half of the media was removed and replaced with fresh mTeSR™-1. On the final day, the cells from the spinner flasks were harvested. First, the media was removed, followed by a PBS wash, followed by the addition of 7 mL of Accutase™ which was gently stirred and returned to the incubator for six minutes. The suspended cells were removed and the carriers were washed with PBS to remove the remaining cells. The cells were then centrifuged at 200 g for 5 minutes and re-suspended in mTeSR™-1 for counting via Nucleocounter. Over 3 days, a 1.8-fold expansion with 71% viability was obtained. In a second experiment, a 3.6-fold expansion with 92% viability was obtained over 4 days.

In another example, Prototype II (Cytodex® I) microcarriers were coated with 7 mL of Matrigel™ (BD) diluted 1:20 in DMEM/F12 for 60 minutes with mixing every 20 minutes, followed by 0 or 1 washes with PBS. CT2 cells were seeded onto the Matrigel™-coated carriers in the spinner flask at a concentration of 8×106 cells/220 cm² carriers in 50 ml mTeSR-1. The cells were seeded with continuous stirring at 25 rpm for 15 minutes, followed by a 1 minute on/45 minutes off cycle at 25 rpm over the course of four days after seeding. FIG. 9 B shows CT2 cells grown on commercial microcarrier of prototype II in spinner flask. On the second day after seeding, half of the media was removed and replaced with fresh mTeSR™-1. On the final day, the spinner flasks were harvested. First, the media was removed, followed by a PBS wash, followed by the addition of 7 mL of Accutase™ which was gently stirred and returned to the incubator for six minutes. The suspended cells were removed and the carriers were washed with PBS to remove the remaining cells. The cells were then centrifuged at 200 g for 5 minutes and re-suspended in mTeSR™-1 for counting via Nucleocounter. Over 4 days, a 1.2-fold expansion with 45% viability was obtained.

In another example, Prototype III microcarriers were coated with 7 mL of Matrigel™ diluted 1:20 in DMEM/F12 for 60 minutes with mixing every 20 minutes, followed by 0 or 1 wash with PBS. CT2 cells were seeded onto the Matrigel™-coated carriers in the spinner flask at a concentration of 4×10⁶ cells/100 cm² carriers in 50 ml mTeSR-1. The cells were seeded with continuous stirring at 40 rpm for 15 minutes, followed by a 1 minute on/45 minutes off cycle at 40 rpm over the course of four days after seeding. FIG. 9 C shows CT2 cells grown on commercial microcarrier of prototype III in spinner flask. On the second day after seeding, half of the media was removed and replaced with fresh mTeSR-1. On the final day, the spinner flasks were harvested. First, the media was removed, followed by a PBS wash, followed by the addition of 7 mL of Accutase™ which was gently stirred and returned to the incubator for six minutes. The suspended cells were removed and the carriers washed with PBS to remove the remaining cells. The cells were then centrifuged at 200 g for 5 minutes and re-suspended in mTeSR™-1 for counting via Nucleocounter. Over 3 days, a 0.8-fold expansion with 66% viability was obtained. FIG. 9 D shows CT2 cells grown on carrier of the invention in a spinner flask.

TABLE 4

Characterization of cells grown on different carriers

| Carrier type | Carrier clump or cell-bridging | Visibility of cells under Microscope | Shear | Separating carriers from cells | Fold expansion | Viability |
|---|---|---|---|---|---|---|
| GRC | No | Good | low | Easy | 3.6 X, 3 days 6.2 X, 4 days (n > 30) | 90% |
| Prototype I | Yes | Good | high | Difficult | 1.8X, 3 days (n = 1) | 71% |
| Prototype II | Yes | Poor | high | Difficult | 1.2X, 4 days (n = 2) | 40-55% |
| Prototype III | Yes | very poor | high | Difficult | 0.8X, 3 days (n = 1) | 66% |

Example 14

Cell Growth on Gamma Sterilized Carriers

Carriers were embossed on both sides with 650 nm pitch waffle pattern (450 nm square well size with a depth of 200 μm) and cut into hexagonal pieces (0.25" edge-to-edge width) via rotary cutting. Carriers were plasma treated as 1135 g batch in a custom-made rotating drum plasma system with a central rod anode. The plasma was generated at 500 W with a 1000 sccm flow of $O_2$ for 18 minutes with a rotation rate of ~5 rpm. Carriers were stored at room temperature and ambient humidity for at least one month before washing. Carriers were washed (~300 g/batch) with 70% Ethanol/$H_2O$ (2000 g×3 washes). The carriers were agitated in the wash solution, drained and dried centrifugally thrice, prior to overnight drying in a vacuum oven (40° C., 5 Torr) for at least 4 hours (or until mass loss ceased). Aliquots were massed (1.17 g/batch) in polypropylene 50 mL centrifuge tubes (Corning). Aliquots were heat sealed in a low density polyethylenepolyethylene (LDPE) bag and shipped for gamma sterilization (25 kGy). After gamma sterilization, the carriers were delivered to the biology lab for cell culture and re-suspended in the medium.

The carriers were transferred under sterile conditions to a Corning 125 mL disposable spinner flask (#3152). The carriers were then coated with 7 mL of Matrigel™ (BD) diluted 1:20 in DMEM/F12 for 60 minutes with mixing every 20 minutes, followed by 0 or 1 washes with phosphate buffered saline (PBS).

Human embryonic stem cells (CT-2 cell line, University of Connecticut) were grown on a Matrigel™ (BD) coated 6-well tissue culture polystyrene plate for four passages prior to this experiment. Cells were washed once with PBS and treated with Accutase™ (MP) for three minutes at 37° C. Cells were centrifuged at 200 G for 5 minutes and re-suspended in mTeSR-1 medium. Cells were counted on a NucleoCounter NC-100 (Chemometec, Denmark). The cells were seeded (intermittent stirring at 40 rpm with a 1 minute on/10 minute off cycle for one hour) onto the Matrigel™-coated carriers in the spinner flask at a concentration of $3×10^6$ cells/100 $cm^2$ projected surface area (1.17 g aliquot) in 50 ml mTeSR™-1. The cells were cultured with 1 minute of stirring at 25 rpm followed by 45 minutes static over the course of three days after seeding. Starting on day 2, half of the media was removed and replaced with fresh mTeSR™-1. On the final day, the cells were harvested from the spinner flasks. First, the media was removed, followed by a PBS wash, followed by the addition of 7 mL of Accutase™ which was gently stirred and returned to the incubator for six minutes. The suspended cells were removed and the carriers were washed with PBS to remove the remaining cells. The cells were then centrifuged at 200 g for 5 minutes and re-suspended in mTeSR-1 for counting via Nucleocounter. $32.6×10^6$ live cells were recovered, for a fold expansion of 10.9 with a viability of 93.7%.

Example 15

Cell Growth on Non Plasma Treated Carriers

Carriers were embossed on both sides with 650 nm pitch waffle pattern (450 nm square well size with a depth of 200 nm) and cut into hexagonal pieces (0.25" edge-to-edge width) via rotary cutting. Carriers were stored at room temperature and ambient humidity for at least one month before aliquots were prepared (1.17 g/batch) in polypropylene 50 mL centrifuge tubes (Corning). Each aliquot was washed thrice with isopropanol, four times with 18.2MΩ deionized water and thrice with 70% Ethanol/$H_2O$ (vol./vol.) The final wash solution was left in place and the samples transferred to the biology lab for cell growth.

The carriers were transferred under sterile conditions to a Corning 125 mL disposable spinner flask (#3152). The carriers were then coated with 7 mL of Matrigel™ (BD) diluted 1:20 in DMEM/F12 for 60 minutes with mixing every 20 minutes. Alternatively, the carriers can be coated with Matrigel™ in a conical tube.

Human embryonic stem cells (CT-2 cell line, University of Connecticut) were grown on a Matrigel™ (BD) coated 6-well tissue culture polystyrene plate for seven passages prior to this experiment. Cells were washed once with PBS and treated with Accutase™ (MP) for three minutes at 37° C. Cells were centrifuged at 200 G for 5 minutes and re-suspended in mTeSR-1 medium. Cells were counted on a NucleoCounter NC-100 (Chemometec, Denmark). The cells were seeded (intermittent stirring at 40 rpm with a 1 minute on/10 minute off cycle for one hour) onto the Matrigel™-coated carriers in the spinner flask at a concentration of $3×10^6$ cells/100 $cm^2$ projected surface area (1.17 g aliquot) in 50 ml mTeSR™-1. The cells were cultured with 1 minute of stirring at 25 rpm followed by 45 minutes static over the course of three days after seeding. Starting on day 2, half of the media was removed and replaced with fresh mTeSR™ 1. Individual carriers were removed and imaged by microscopy for the presence of colonies, as shown in FIGS. 10 A to 10 D. Numerous colonies were observed on the non-plasma treated, Matrigel™ coated carriers. On the final day, the spinner flasks were harvested. First, the media was removed, followed by a PBS wash, followed by the addition of 7 mL of Accutase™ which was gently stirred and returned to the incubator for six minutes. The suspended cells were removed and the carriers washed with PBS to remove the remaining cells. The cells were then centrifuged at 200 g for 5 minutes and re-suspended in mTeSR™-1 for counting via Nucleocounter. $9.7×10^6$ live cells were recovered, for a 3.2 fold expansion. FIGS. 10 A to 10 D are a series of optical microscopy images demonstrating human CT2 pluripotent stem cell seeding and expansion on non-plasma treated carriers of the invention coated with Matrigel™ in spinner flasks. Cells were expanded over 4 days in spinner flasks and have normal pluripotent stem cell colony morphology. Colony growth on day 2 after seeding is shown on non-plasma treated carriers (FIG. 10 A) and plasma treated carriers (FIG. 10 B). Colony growth on non-plasma treated carriers on day 4 after seeding is shown in FIG. 10 C (40× magnification) and FIG. 10 D (100× magnification).

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A carrier for expansion of pluripotent stem cells, comprising:
 a planar substrate disc comprising a first surface and a second surface opposing the first surface and a plurality of structured indentations formed in the first surface and the second surface;
 wherein the first surface and the second surface are modified with gas plasma treatment, and
 wherein the planar substrate disc has a length at least about 0.2 mm, a width at least about 0.2 mm, and a height in a range from about 0.05 mm to 1.2 mm, wherein the height extends from a highest point of the first surface through the planar substrate disc and to a highest point of the second surface and each of the structured indentations has a major axis in a range from about 0.1 mm to 0.5 mm, a minor axis in a range from about 0.1 mm to 0.5 mm and a depth in a range from about 0.025 mm to 0.5 mm and wherein a first structured indentation of the plurality of structured indentations is aligned with a second structured indentation of the plurality of structured indentations in the planar substrate disc such that respective bottoms of the first structured indentation and the second structured indentation are separated by a portion of the planar substrate disc.

2. The carrier of claim 1, wherein the first surface and the second surface are configured for expansion of pluripotent stem cells.

3. The carrier of claim 1, wherein the gas plasma treatment comprises plasma treatment with one or more gases comprising oxygen, nitrogen, amonia, carbon dioxide or combinations thereof.

4. The carrier of claim 1, wherein the gas plasma treatment comprises oxygen plasma treatment.

5. The carrier of claim 1, further comprising a biomolecular coating disposed on one or more of the first surface or the second surface.

6. The carrier of claim 5, wherein the biomolecular coating comprises proteins or peptides.

7. The carrier of claim 5, wherein the biomolecular coating comprises proteins.

8. The carrier of claim 7, wherein the proteins comprise collagen, vitronectin, fibronectin, laminin, recombinant collagen, recombinant vitronectin, recombinant e-cadherin or combinations thereof.

9. The carrier of claim 5, wherein the biomolecular coating comprises synthetic peptides.

10. The carrier of claim 5, wherein the biomolecular coating comprises extracellular matrix (ECM) proteins, proteoglycans, factors derived from a mouse sarcoma cell line, or combinations thereof.

11. The carrier of claim 5, wherein the biomolecular coating forms a cytophilic surface.

12. The carrier of claim 1, wherein each of the structured indentations comprises a cross sectional profile of polygonal, circular, or elliptical shape.

13. The carrier of claim 1, wherein each of the structured indentations has an aspect ratio in a range from about 0.1 to about 1.5.

14. The carrier of claim 1, wherein the carrier is made of glass, a polymer, a ceramic, a metal, or combinations thereof.

15. The carrier of claim 1, wherein the carrier is made of dextran, silicone, polyester, polycarbonate, polyamide, polyurethane, olefin polymer, or polyacrylate polymer.

16. The carrier of claim 1, wherein the carrier is made of polystyrene.

17. The carrier of claim 1, having a perimeter that is triangular, rectangular, square, pentagonal, hexagonal, circular, or elliptical.

18. A cell culture system comprising at least one of the carrier of claim 1.

19. The cell culture system of claim 18, wherein the cell culture system is a bioreactor.

20. The cell culture system of claim 19, wherein the bioreactor comprises a fluid having a forced convective fluid motion.

21. The cell culture system of claim 20, wherein the bioreactor is a stirred tank bioreactor, or a reactor with rocking or rolling motion.

22. A kit for culturing cells, comprising a disposable housing pre-loaded with the carrier of claim 1.

23. The kit of claim 22, wherein the disposable housing comprises a bag, a flask, a tube, a petridish, or a bottle.

24. A carrier for expansion of pluripotent stem cells, comprising:
a planar substrate comprising a first surface and a second surface opposing the first surface and a plurality of structured indentations on the first surface and the second surface;
wherein the first surface and the second surface comprise a biomolecular coating,
wherein the planar substrate has a length at least about 0.2 mm, a width at least about 0.2 mm, and a height in a range from about 0.05 mm to 1.2 mm, wherein the height extends from a highest point of the first surface through the planar substrate and to a highest point of the second surface, and wherein each of the structured indentations has a major axis in a range from about 0.1 mm to 0.5 mm, a minor axis in a range from about 0.1 mm to 0.5 mm and a depth in a range from about 0.025 mm to 0.5 mm and wherein a first structured indentation of the plurality of structured indentations is aligned with a second structured indentation of the plurality of structured indentations in the planar substrate such that respective bottoms of the first structured indentation and the second structured indentation are separated by a portion of the planar substrate; and
a plurality of pluripotent stem cells disposed in a least one of the plurality of structured indentations.

25. The carrier of claim 24, wherein the biomolecular coating comprises proteins or peptides.

26. A carrier for expansion of pluripotent stem cells, comprising:
a planar substrate comprising a first surface and a second surface opposing the first surface modified with one or more of corona discharge treatment, gas plasma treatment, or chemical functionalization to form modified surfaces and a plurality of structured indentations on the first surface and the second surface;
a biomolecular coating disposed on the first or second surface,
wherein the carrier has a length at least about 0.2 mm, a width at least about 0.2 mm, and a height in a range from about 0.05 mm to 1.2 mm wherein the height extends from a highest point of the first surface through the planar substrate and to a highest point of the second surface, and each of the structured indentations has a major axis in a range from about 0.1 mm to 0.5 mm, a minor axis in a range from about 0.1 mm to 0.5 mm, and a depth in a range from about 0.025 mm to about 0.5 mm and wherein a first structured indentation of the plurality of structured indentations is aligned with a second structured indentation of the plurality of structured indentations in the planar substrate such that respective bottoms of the first structured indentation and the second structured indentation are separated by a portion of the planar substrate; and
a plurality of pluripotent stem cells disposed in at least one of the plurality of indentations.

27. The carrier of claim 26, wherein the gas plasma treatment comprises plasma treatment with one or more of the gases comprising oxygen, nitrogen, amonia, carbon dioxide, or combinations thereof.

* * * * *